United States Patent
Schlosser et al.

(10) Patent No.: US 11,179,222 B2
(45) Date of Patent: Nov. 23, 2021

(54) RAPIDLY REPOSITIONABLE POWERED SUPPORT ARM

(71) Applicant: SoniTrack Systems, Inc., Menlo Park, CA (US)

(72) Inventors: Jeffrey Schlosser, Menlo Park, CA (US); Christopher A Tacklind, Menlo Park, CA (US)

(73) Assignee: SoniTrack Systems, Inc., Menlo Park, CA (US)

( * ) Notice: Subject to any disclaimer, the term of this patent is extended or adjusted under 35 U.S.C. 154(b) by 0 days.

(21) Appl. No.: 16/877,023

(22) Filed: May 18, 2020

(65) Prior Publication Data

US 2020/0352676 A1   Nov. 12, 2020

Related U.S. Application Data

(63) Continuation of application No. 15/560,894, filed as application No. PCT/US2016/021076 on Mar. 4, 2016, now Pat. No. 10,687,915.
(Continued)

(51) Int. Cl.
*A61B 90/50* (2016.01)
*F16M 13/02* (2006.01)
(Continued)

(52) U.S. Cl.
CPC ........... *A61B 90/50* (2016.02); *F16M 13/022* (2013.01); *A61B 5/026* (2013.01); *A61B 90/06* (2016.02);
(Continued)

(58) Field of Classification Search
None
See application file for complete search history.

(56) References Cited

U.S. PATENT DOCUMENTS

| | | | |
|---|---|---|---|
| 2,752,116 A | 6/1956 | Minnis | |
| 3,910,538 A | 10/1975 | Baitella | |

(Continued)

FOREIGN PATENT DOCUMENTS

| | | |
|---|---|---|
| CN | 107614817 A | 1/2018 |
| DE | 102015104810 A1 | 9/2016 |

(Continued)

OTHER PUBLICATIONS

US 10,792,124 B2, 10/2020, Billard et al. (withdrawn)
(Continued)

*Primary Examiner* — Steven M Marsh
(74) *Attorney, Agent, or Firm* — Schwegman Lundberg & Woessner, P.A.

(57) ABSTRACT

A repositionable, lockable support arm assembly for surgical and other tools includes a base arm having a lower end and an upper end, a distal arm having a proximal end and a distal end, and a central joint, typically a rotational joint, directly or indirectly linking the upper end of the base arm to the proximal end of the distal arm. A lower joint, typically a spherical joint, is positioned at the lower end of the base arm, and an upper joint, also typically a spherical joint, is located at the distal end of the distal arm. A locking mechanism is coupled to the base arm at a location above the lower joint and is configured to simultaneously deliver locking forces to the lower joint, to the rotational joint, and to the upper joint. The kicking mechanism usually includes a powered, bilateral force generator for actuating the locking mechanism.

20 Claims, 36 Drawing Sheets

Related U.S. Application Data

(60) Provisional application No. 62/139,535, filed on Mar. 27, 2015, provisional application No. 62/169,440, filed on Jun. 1, 2015, provisional application No. 62/213,509, filed on Sep. 2, 2015, provisional application No. 62/280,631, filed on Jan. 19, 2016.

(51) Int. Cl.
*A61B 90/57* (2016.01)
*A61B 90/00* (2016.01)
*A61B 5/026* (2006.01)
*A61B 17/00* (2006.01)

(52) U.S. Cl.
CPC ............... *A61B 2017/00119* (2013.01); *A61B 2090/065* (2016.02); *A61B 2090/508* (2016.02); *A61B 2090/571* (2016.02); *F16M 2200/022* (2013.01)

(56) References Cited

U.S. PATENT DOCUMENTS

| | | | |
|---|---|---|---|
| 4,402,481 | A | 9/1983 | Sasaki |
| 4,514,117 | A | 4/1985 | Scott |
| 5,779,209 | A | 7/1998 | Rello |
| 5,824,085 | A | 10/1998 | Sahay et al. |
| 6,467,362 | B2 | 10/2002 | Erikson |
| 6,575,653 | B1 | 6/2003 | Kräuter |
| 6,860,877 | B1 | 3/2005 | Sanchez et al. |
| 7,611,378 | B1 | 11/2009 | Brekosky et al. |
| 9,592,096 | B2 | 3/2017 | Maillet et al. |
| D878,585 | S | 3/2020 | Garcia |
| 10,687,792 | B2 | 6/2020 | Garcia et al. |
| 10,687,915 | B2 | 6/2020 | Schlosser et al. |
| 10,772,704 | B2 | 9/2020 | Garcia et al. |
| 10,835,345 | B2 | 11/2020 | Billard et al. |
| D910,848 | S | 2/2021 | Garcia |
| 2002/0017857 | A1 | 2/2002 | Hashimoto et al. |
| 2002/0074472 | A1 | 6/2002 | Gaida et al. |
| 2002/0117857 | A1 | 8/2002 | Eckstein |
| 2002/0177857 | A1 | 11/2002 | Otsuka et al. |
| 2002/0188293 | A1 | 12/2002 | Manzo |
| 2004/0172012 | A1 | 9/2004 | Otsuka et al. |
| 2008/0142658 | A1* | 6/2008 | Jurja .................. A47B 21/0314 248/220.21 |
| 2008/0164395 | A1* | 7/2008 | Chang .................. F16M 11/105 248/276.1 |
| 2010/0020002 | A1 | 1/2010 | Van Woudenberg et al. |
| 2010/0200002 | A1 | 8/2010 | Orban, III et al. |
| 2011/0290855 | A1 | 12/2011 | Moore et al. |
| 2011/0315843 | A1 | 12/2011 | Hung |
| 2012/0182134 | A1 | 7/2012 | Doyle |
| 2012/0265240 | A1 | 10/2012 | Ganske et al. |
| 2013/0187022 | A1 | 7/2013 | Duportal et al. |
| 2013/0292522 | A1* | 11/2013 | Sears ................. F16M 11/2092 248/118 |
| 2013/0299658 | A1* | 11/2013 | Hung ..................... F16M 11/24 248/276.1 |
| 2014/0343572 | A1 | 11/2014 | Windolf et al. |
| 2014/0379038 | A1 | 12/2014 | Dogramadzi et al. |
| 2015/0032215 | A1 | 1/2015 | Slamin et al. |
| 2015/0100066 | A1 | 4/2015 | Kostrzewski et al. |
| 2016/0081753 | A1 | 3/2016 | Kostrzewski |
| 2016/0151120 | A1 | 6/2016 | Kostrzewski et al. |
| 2016/0270780 | A1 | 9/2016 | Hall et al. |
| 2017/0034021 | A1 | 11/2017 | Chuang |
| 2017/0340389 | A1 | 11/2017 | Otto et al. |
| 2017/0360521 | A1 | 12/2017 | Johnson |
| 2018/0116758 | A1 | 5/2018 | Schlosser et al. |
| 2018/0256217 | A1 | 9/2018 | Dekel et al. |
| 2018/0360544 | A1 | 12/2018 | Vanheule et al. |
| 2019/0167356 | A1 | 6/2019 | Britton et al. |
| 2019/0274665 | A1 | 9/2019 | Garcia |
| 2019/0274777 | A1 | 9/2019 | Garcia et al. |
| 2019/0274778 | A1 | 9/2019 | Billard et al. |
| 2019/0274780 | A1 | 9/2019 | Nowatschin et al. |
| 2020/0281576 | A1 | 9/2020 | Garcia et al. |

FOREIGN PATENT DOCUMENTS

| | | | |
|---|---|---|---|
| EP | 2777539 | A2 | 9/2014 |
| EP | 2143372 | B1 | 12/2014 |
| EP | 3274521 | A1 | 1/2018 |
| JP | S57144399 | A | 9/1982 |
| JP | 63280911 | A | 11/1988 |
| JP | S63280911 | A | 11/1988 |
| JP | 2001187064 | A | 7/2001 |
| JP | 2018509273 | A | 4/2018 |
| JP | 2021062232 | A | 4/2021 |
| WO | WO-9639944 | A1 | 12/1996 |
| WO | WO-2014108898 | A1 | 7/2014 |
| WO | WO-2016160272 | A1 | 10/2016 |
| WO | WO-2017017443 | A1 | 2/2017 |
| WO | WO-2017151887 | A1 | 9/2017 |
| WO | WO-2019177567 | A1 | 9/2019 |
| WO | WO-2019177569 | A1 | 9/2019 |
| WO | WO-2019177570 | A1 | 9/2019 |

OTHER PUBLICATIONS

"3840 Series Holder", Fisso—Rail-mounted instrument holding arm / articulated, [Online], [Accessed Oct. 16, 2017], Retrieved from the Internet: <URL: http://www.medicalexpo.com/prod/fisso/product-67723-681104.html>, 3 pgs.

"3D-Arm™", Elekta—Minimally invasive surgery instrument holding arm, [Online]. [Accessed Oct. 16, 2017], Retrieved from the Internet: <URL: http://www.medicalexpo.com/prod/elekta/product-70692-509376.html>, 8 pgs.

"ALLY Uterine Positioning System", Cooper Surgical, [Online], [Accessed Oct. 16, 2017], Retrieved from the Internet: <URL: https://www.coopersurgical.com/Products/Detail/ALLY-Uterine-Positioning-System>, 2 pgs.

"Anatomical Shoulder Fracture System", Zimmer Surgical Technique, 97-4223-003-00 Rev. 1, (2005), 24 pgs.

"Anatomical Shoulder Glenoid", Zimmer Surgical Technique, (2014), 12 pgs.

"U.S. Appl. No. 15/560,894, Final Office Action dated Nov. 29, 2019", 8 pgs.

"U.S. Appl. No. 15/560,894, Non Final Office Action dated May 16, 2019", 9 pgs.

"U.S. Appl. No. 15/560,894, Notice of Allowance dated Feb. 13, 2020", 8 pgs.

"U.S. Appl. No. 15/560,894, Preliminary Amendment filed Sep. 22, 2017", 7 pgs.

"U.S. Appl. No. 15/560,894, Response filed Jan. 28, 2020 to Final Office Action dated Nov. 29, 2019", 7 pgs.

"U.S. Appl. No. 15/560,894, Response filed Mar. 21, 2019 to Restriction Requirement dated Dec. 31, 2018", 9 pgs.

"U.S. Appl. No. 15/560,894, Response filed Aug. 16, 2019 to Non Final Office Action dated May 16, 2019", 11 pgs.

"U.S. Appl. No. 15/560,894, Restriction Requirement dated Dec. 31, 2018", 7 pgs.

"U.S. Appl. No. 15/560,894, Supplemental Preliminary Amendment filed Sep. 29, 2017", 7 pgs.

"U.S. Appl. No. 15/918,531, Corrected Notice of Allowability dated May 20, 2020", 2 pgs.

"U.S. Appl. No. 15/918,531, Non Final Office Action dated Sep. 26, 2019", 12 pgs.

"U.S. Appl. No. 15/918,531, Notice of Allowance dated Feb. 19, 2020", 11 pgs.

"U.S. Appl. No. 15/918,531, Response filed Dec. 26, 2019 to Non Final Office Action dated Sep. 26, 2019", 12 pgs.

"U.S. Appl. No. 15/919,150, Non Final Office Action dated Jan. 13, 2020", 10 pgs.

"U.S. Appl. No. 15/919,150, Notice of Allowance dated May 12, 2020", 5 pgs.

(56) References Cited

OTHER PUBLICATIONS

"U.S. Appl. No. 15/919,150, Response filed Apr. 10, 2020 to Non Final Office Action dated Jan. 13, 2020", 11 pgs.
"U.S. Appl. No. 15/919,150, Supplemental Notice of Allowability dated Jul. 6, 2020", 2 pgs.
"U.S. Appl. No. 15/919,150, Supplemental Notice of Allowability dated Jul. 29, 2020", 2 pgs.
"U.S. Appl. No. 15/919,161, Corrected Notice of Allowability dated Jul. 29, 2020", 2 pgs.
"U.S. Appl. No. 15/919,161, Final Office Action dated Feb. 19, 2020", 7 pgs.
"U.S. Appl. No. 15/919,161, Non Final Office Action dated Sep. 26, 2019", 18 pgs.
"U.S. Appl. No. 15/919,161, Notice of Allowance dated Jun. 4, 2020", 9 pgs.
"U.S. Appl. No. 15/919,161, Response filed May 18, 2020 to Final Office Action dated Feb. 19, 2020", 10 pgs.
"U.S. Appl. No. 15/919,161, Response filed Dec. 26, 2019 to Non Final Office Action dated Sep. 26, 2019", 13 pgs.
"U.S. Appl. No. 16/210,787, Response filed Jun. 15, 2020 to Restriction Requirement dated Apr. 16, 2020", 6 pgs.
"U.S. Appl. No. 16/210,787, Restriction Requirement dated Apr. 16, 2020", 5 pgs.
"U.S. Appl. No. 16/879,500, Preliminary Amendment filed Jun. 19, 2020", 6 pgs.
"U.S. Appl. No. 29/640,121, Corrected Notice of Allowability dated Jan. 21, 2020", 4 pgs.
"U.S. Appl. No. 29/640,121, Notice of Allowance dated Nov. 5, 2019", 8 pgs.
"U.S. Appl. No. 29/721,682, Non Final Office Action dated Jun. 23, 2020".
"ASSISTO Arm System", Geomed GMBH, [Online], [Accessed Oct. 16, 2017], Retrieved from the Internet: <URL: http://www.geomed.de/index.php?id=65&L=1>, 1 pg.
"Atlas™ Flex Arm System", Axcess Surgical, [Online], [Accessed Oct. 16, 2017], Retrieved from the internet: <URL: http://www.axcesssurgical.com/axcess-surgical-innovations-products/atlas-flex-arm-system/>, 5 pgs.
"Atlas™ Rigid Arm System", Axcess Surgical, [Online], [Accessed Oct. 16, 2017], Retrieved from the Internet: <URL: http://www.axcesssurgical.com/axcess-surgical-innovations-products/atlas-rigid-arm-system/>, 6 pgs.
"Australian Application Serial No. 2016243292, First Examination Report dated Apr. 7, 2020", 4 pgs.
"Australian Application Serial No. 2016243292, Response filed Jun. 29, 2020 to First Examination Report dated Apr. 7, 2020", 30 pgs.
"Bookler® StrongArm™ Holder", Mediflex, [Online], [Accessed Nov. 2, 2017], Retrieved from the Internet: <URL: http://www.mediflex.com/product/bookler-strongarm-holder-and-positioner-set-12-30cm-post/>, (2015), 4 pgs.
"Canadian Application Serial No. 3,002,354, Office Action dated Apr. 27, 2020", 3 pgs.
"Canadian Application Serial No. 3,002,354, Office Action dated Jul. 4, 2019", 4 pgs.
"Canadian Application Serial No. 3,002,354, Response filed Dec. 20, 2019 to Office Action dated Jul. 4, 2019", 14 pgs.
"Chinese Application Serial No. 201680027778.9, Office Action dated Feb. 6, 2020", with English translation, 6 pages.
"Chinese Application Serial No. 201680027778.9, Office Action dated Jun. 12, 2020", with English translation, 18 pages.
"Chinese Application Serial No. 201680027778.9, Office Action dated Jul. 12, 2019", w/English Translation, 20 pgs.
"Chinese Application Serial No. 201680027778.9, Response filed Mar. 19, 2020 to Office Action dated Feb. 6, 2020", with English claims, 8 pages.
"Chinese Application Serial No. 201680027778.9, Response filed Jul. 15, 2020 to Office Action dated Jun. 12, 2020", with English claims, 71 pages.
"Chinese Application Serial No. 201680027778.9, Response filed Oct. 31, 2019 to Office Action dated Jul. 12, 2019", (w/English Claims), 15 pgs.
"Comprehensive Segmental Revision System, Proximal Humeral Reconstruction, Distal Humeral Reconstruction, Total Humeral Reconstruction", Zimmer Biomet Surgical Technique, 0097.1-US-en-REV0416, (2016), 68 pgs.
"EndoArm", Olympus, [Online], [Accessed Nov. 2, 2017], Retrieved from the Internet: <URL: https://www.olympus.co.jp/jp/news/2003b/nr030925endoj.html>, (Sep. 25, 2003), 4 pgs.
"EndoBoy", LUT—Pneumatic Arm, Grecco, 8 pgs.
"EndoCrane", Karl Storz—LEROY Retractors for Laparoscopic Colorectal Surgery, [Online], [Accessed Oct. 16, 2017], Retrieved from the Internet: <URL: https://www.karlstorz.com/cps/rde/xbcr/karlstorz_assets/assets/2193800.pdf>, 16 pgs.
"European Application Serial No. 16773696.6, Extended European Search Report dated Nov. 19, 2018", 8 pgs.
"European Application Serial No. 16773696.6, Response filed Jun. 4, 2018 to Office Action dated Nov. 22, 2018".
"European Application Serial No. 16773696.6, Response filed Jun. 17, 2019 to Extended European Search Report dated Nov. 19, 2018", 18 pgs.
"European Application Serial No. 18210813.4, Extended European Search Report dated Apr. 12, 2019", 7 pgs.
"Genzyme Remote Surgical Retractor Arm Hands Free Pneumatic System", Renix Interational/Alibaba.com Copyright 1999-2017, [Online], [Accessed Nov. 2, 2017], Retrieved from the Internet: <URL: http://renix.trustpass.alibaba.com/product/50001078652-219532304/Genzyme_Remote_Surgical_Retractor_Arm_Hands_Free_Pneumatic_System.html>, 2 pgs.
"Helping Hand", Fraunhofer IPA—The helping hand in the operation room Research News, [Online], [Accessed Oct. 16, 2017], Retrieved from the Internet: <URL: https://www.fraunhofer.de/en/press/research-news/2015/november/helping-hand-in-the-operation-room.html>, (Nov. 2015), 2 pgs.
"International Application Serial No. PCT/US2016/021076, International Preliminary Report on Patentability dated Oct. 12, 2017", 11 pgs.
"International Application Serial No. PCT/US2016/021076, International Search Report dated Aug. 11, 2016", 4 pgs.
"International Application Serial No. PCT/US2016/021076, Invitation to Pay Add'l Fees and Partial Search Report dated May 25, 2016", 2 pgs.
"International Application Serial No. PCT/US2016/021076, Written Opinion dated Aug. 11, 2016", 8 pgs.
"International Application Serial No. PCT/US2018/021988, International Search Report dated Dec. 20, 2018", 4 pgs.
"International Application Serial No. PCT/US2018/021988, Written Opinion dated Dec. 20, 2018", 6 pgs.
"International Application Serial No. PCT/US2018/022004, International Search Report dated Feb. 14, 2019", 8 pgs.
"International Application Serial No. PCT/US2018/022004, Invitation to Pay Additional Fees dated Dec. 19, 2018", 15 pgs.
"International Application Serial No. PCT/US2018/022004, Written Opinion dated Feb. 14, 2019", 14 pgs.
"International Application Serial No. PCT/US2018/022006, International Search Report dated Feb. 8, 2019", 8 pgs.
"International Application Serial No. PCT/US2018/022006, Invitation to Pay Additional Fees dated Dec. 12, 2018", 16 pgs.
"International Application Serial No. PCT/US2018/022006, Written Opinion dated Feb. 8, 2019", 15 pgs.
"IronIntern", Automated Medical, [Online], [Accessed Oct. 16, 2017], Retrieved from the Internet: <URL: http://ironintem.com/iron-intern%E2%84%A2>, 1 pg.
"Japanese Application Serial No. 2018-501138, Notification of Reasons for Refusal dated Nov. 5, 2019", (w/English Translation), 15 pgs.
"Japanese Application Serial No. 2018-501138, Response filed Apr. 22, 2020 to Notification of Reasons for Refusal dated Nov. 5, 2019", with English claims, 15 pgs.
"Jarit Endoscope Holder", Integra, [Online], [Accessed Oct. 16, 2017], Retrieved from: <URL: https://www.integralife.com/endoscope-

(56) References Cited

OTHER PUBLICATIONS instrument-holder-set/product/surgical-instruments-hospitals-surgery-centers-tissue-banks-jarit-laparoscopic-endoscopes-endoscope-instrument-holder-set>, 18 pgs.

"M-Trac", Aesculap / B Braun, [Online], [Accessed—Oct. 16, 2017], Retrieved from the Internet: <URL: https://www.bbraun.com/en/products/b/m-trac.html>, 2 pgs.

"Martin's Arm", Hayden Medical (& others), [Online], [Accessed Oct. 16, 2017], Retrieved from the Internet: <URL: http://haydenmedical.com/surgical-retractors-martins-arm-retractors/>, 2 pgs.

"Mechanical Arm—Mod. 8470", Ansabere Surgical, [Online], [Accessed Oct. 16, 2017], Retrieved from the Internet: <URL: http://www.ansaberesurgical.com/en/productos/brazos-mecanicos/brazo-mecanico-mod-8470/>, 5 pgs.

"Phantom ML", TeDan Surgical Innovations, [Online], [Accessed Nov. 14, 2017], Retrieved from the Internet: <URL: http://www.tedansurglcal.com/spine/articulating-arms/>, 2 pgs.

"Point Setter", Mitaka Kohki Co., Ltd. Operating / User's Manual Model: PSMS2, (Feb. 14, 2010), 28 pgs.

"PositionOR", Surgical Concept Designs, [Online], [Acessed Nov. 14, 2017], Retrieved from the Internet: <URL: http://surgical-concepts.com/products/PositionOR/>, 1 pg.

"Postioning Arm", Civco—Laparostat™ Kit, [Online], [Accessed Oct. 16, 2017], Retrieved from the Internet: <URL: http://www.civco.com/mmi/resources/ifu/043687.pdf>, 16 pgs.

"SaphLITE | RadLITE", Teleflex Medical, [Online], [Accessed Nov. 14, 2017], Retrieved from the Internet: <URL: https://www.teleflex.com/en/usa/prod_saphlite-radlite.php>, 1 pg.

"Saphlite/Saphlift", Genzyme Surgical Products (Jan. 7, 1999), [Online]. [Accessed Oct. 16, 2017], Retrieved from the Internet: <URL: https://www.accessdata.fda.gov/cdrh_docs/pdf/K990062.pdf>, 5 pgs.

"Speed-Tract", Integra—Table Mounted Speed—Tract Retractor System, [Online], [Accessedd Oct. 16, 2017], Retrieved from the Internet: <URL: http://occ.integralife.com/products%2Fpdfs%2Fintegra%20table%20mounted%20speed-tract%20retractor%20system%20brochure.pdf>, 6 pgs.

"Spider2 Limb Positioner", Smith & Nephew, [Online], [Accessed Nov. 14, 2017], Retrieved from the Internet: <URL: http://www.smith-nephew.com/new-zealand/advanced-surgical-devices/key-products/sports-medicine/spider2-limb-positioner-for-shoulder--hip--knee--/>, 2 pgs.

"Spine Endoscope & Endoscope Holder", Maxer, [Online], [Accessed Nov. 2, 2017], Retrieved from the Internet: <URL: http://www.maxerendoscopy.com/index.php?option=com_content&view=article&id=190:spine-endoscope-endoscope-holder&catid=81:spine-endoscopy&Itemid=858>, (2013).

"SurgiAssist Camera Holder", SurgiToolsMIS, [Online], [Acessed Nov. 14, 2017], Retrieved from the Internet: <URL: https://www.surgitools.com/surgiassist-camera-holder.html>, 4 pgs.

"Synaptive BrightMatter Drive Robotic Surgical Video Arm System", Synaptive, [Online], [Accessed Nov. 14, 2017], Retrieved from the Internet: <URL: https://www.medgadget.com/2016/05/synaptive-brightmatter-drive-robotic-surgical-videoarm-system.html>, 3 pgs.

"TEE Transducer Holder", Civco, [Online], [Accessed Oct. 16, 2017], Retrieved from the Internet: <URL: http://www.civco.com/mmi/resources/product-support/TEE-Holder-Brochure_2008P-2339-Rev-2_low-res-8I9rv5.pdf>, 8 pgs.

"The Freehand System", Freehand—V1.2, [Online], [Acessed Oct. 16, 2017], Retrieved from the Internet: <URL: http://freehandsurgeon.com/Products/Detail?id=2>, 3 pgs.

"TiREX® Retractor System", Orion Surgical, [Online], [Accessed Nov. 2, 2017], Retrieved from the Internet: <URL: http://www.orion-surgical.com/english/tirex-retractor-system/components-of-the-tirex.html>. (2017), 2 pgs.

"TRIMANO 3D Support Arm", Maquet, [Online], [Accessed Oct. 16, 2017], Retrieved from the Internet: <URL: https://www.maquet.com/int/products/trimano-3d-support-arm/>, 3 pgs.

"UniARM Surgical Support System", MITAKA KOHKI Co., Ltd. Operating / User Manual Version 1.1, [Online]. [Accessed Nov. 2, 2017]. Retrieved from the Internet: <URL: http://mitakausa.com/uniarm/>, (Mar. 20, 2009), 19 pgs.

"Unitrac Retraction & holding system for open & minimally invasive surgery", Aesculap Surgical Technologies—Surgical Instruments, (2010), 12 pgs.

"Unitrac® Pneumatic Holding Arm", Aesculap / B Braun, [Online], [Accessed Oct. 16, 2017], Retrieved from the Internet: <URL: https://www.bbraun.com/en/products/b/unitrac-pneumaticholdingarm.html>, 3 pgs.

"Vertek Articulating Arm", Medtronic—Copyright 2013, [Online]. [Accessed Nov. 2, 2017], Retrieved from the Internet: <URL: http://global.medtronic.com/xg-en/healthcare-professionals/products/neurological/surgical-navigation-imaging/neurosurgery-imaging-surgical-navigation/surgical-procedures.html>, 2 pgs.

"VIKY", Endocontrol Medical, [Online], [Accessed 2014], Retrieved from the Internet: <URL: http://www.endocontrol-medical.com/en/viky-en/>, 5 pgs.

"Wingman Scope Holder", Stryker, [Online], [Accessed Nov. 14, 2017], Retrieved from the Internet: <URL: http://www.stryker.com/cn/products/OREquipmentTelemedicine/EndoscopicSurgeryEquipment/Laparoscopy/Accessories/ScopeHolder/index.htm#>, 3 pgs.

U.S. Appl. No. 16/210,787, filed Dec. 5, 2018, Robotic Shoulder Repair and Reconstruction.

U.S. Appl. No. 16/994,181, filed Aug. 14, 2020, End Effector Coupler for Surgical Arm.

U.S. Appl. No. 17/015,734, filed Sep. 9, 2020, End Effector Coupler for Surgical Arm.

"U.S. Appl. No. 15/919,161, Corrected Notice of Allowability dated Aug. 26, 2020", 4 pgs.

"U.S. Appl. No. 15/919,161, Corrected Notice of Allowability dated Oct. 15, 2020", 2 pgs.

"U.S. Appl. No. 16/210,787, Non Final Office Action dated Sep. 15, 2020", 7 pgs.

"U.S. Appl. No. 16/210,787, Notice of Allowance dated Jan. 4, 2021", 8 pgs.

"U.S. Appl. No. 16/210,787, Response filed Dec. 9, 2020 to Non Final Office Action dated Sep. 15, 2020", 8 pgs.

"U.S. Appl. No. 29/721,682, Corrected Notice of Allowability dated Jan. 19, 2021", 3 pgs.

"U.S. Appl. No. 29/721,682, Examiner Interview Summary dated Sep. 17, 2020", 3 pgs.

"U.S. Appl. No. 29/721,682, Notice of Allowance dated Oct. 5, 2020", 7 pgs.

"U.S. Appl. No. 29/721,682, Response filed Sep. 14, 2020 to Non Final Office Action dated Jun. 23, 2020", 9 pgs.

"Australian Application Serial No. 2016243292, Response filed Sep. 30, 2020 to Subsequent Examiners Report dated Jul. 30, 2020", 30 pgs.

"Australian Application Serial No. 2016243292, Subsequent Examiners Report dated Jul. 30, 2020", 5 pgs.

"Australian Application Serial No. 2016243292, Subsequent Examiners Report dated Oct. 14, 2020", 3 pgs.

"Canadian Application Serial No. 2,980,725, Office Action dated Nov. 12, 2020", 4 pgs.

"Canadian Application Serial No. 2,980,725, Response filed Mar. 11, 2021 to Office Action dated Nov. 12, 2020", 17 pgs.

"Canadian Application Serial No. 3,002,354, Response filed Aug. 4, 2020 to Office Action dated Apr. 27, 2020", 18 pgs.

"International Application Serial No. PCT/US2018/021988, International Preliminary Report on Patentability dated Sep. 24, 2020", 8 pgs.

"International Application Serial No. PCT/US2018/022004, International Preliminary Report on Patentability dated Sep. 24, 2020", 14 pgs.

"International Application Serial No. PCT/US2018/022006, International Preliminary Report on Patentability dated Sep. 24, 2020", 15 pgs.

"Japanese Application Serial No. 2018-501138, Final Notification of Reasons for Refusal dated Sep. 29, 2020", (W/ English Translation), 5 pgs.

(56) References Cited

OTHER PUBLICATIONS

"Japanese Application Serial No. 2018-501138, Response filed Dec. 28, 2020 to Final Notification of Reasons for Refusal dated Sep. 29, 2020", (W/ English Claims), 11 pgs.

"Korean Application Serial No. 10-2017-7030940, Notice of Preliminary Rejection dated Aug. 10, 2020", (W/ English Translation), 13 pgs.

"Korean Application Serial No. 10-2017-7030940, Response filed Oct. 8, 2020 to Notice of Preliminary Rejection dated Aug. 10, 2020", (W/ English Translation), 34 pgs.

"Canadian Application Serial No. 2,980,725, Office Action dated May 21, 2021", 6 pgs.

"European Application Serial No. 18713548.8, Response to Communication pursuant to Rules 161(1) and 162 EPC filed Apr. 29, 2021", 21 pgs.

"European Application Serial No. 18713549.6, Response to Communication pursuant to Rules 161(1) and 162 EPC filed May 20, 2021", 23 pgs.

"Japanese Application Serial No. 2018-501138, Examiners Decision of Final Refusal dated May 11, 2021", (W/ English Translation), 6 pgs.

"Korean Application Serial No. 10-2017-7030940, Notice of Preliminary Rejection dated Feb. 4, 2021", with English translation, 4 pages.

"Korean Application Serial No. 10-2017-7030940, Response filed Mar. 31, 2021 to Notice of Preliminary Rejection dated Feb. 5, 2021", with English translation, 11 pages.

"European Application Serial No. 18713116.4, Response to Communication pursuant to Rules 161(1) and 162 EPC filed Apr. 29, 2021", 20 pgs.

U.S. Appl. No. 17/218,455, filed Mar. 31, 2021, Robotic Shoulder Repair and Reconstruction.

U.S. Appl. No. 15/560,894 U.S. Pat. No. 10,687,915, filed Sep. 22, 2017, Rapidly Repositionable Powered Support Arm.

U.S. Appl. No. 16/210,787, filed Dec. 5, 2018, Robotic Shoulder Repair and Reconstruciton.

U.S. Appl. No. 15/918,531 U.S. Pat. No. 10,687,792, filed Mar. 12, 2018, End Effector Coupler for Surgical Arm.

U.S. Appl. No. 29/640,121 D878,585, filed Mar. 12, 2018, End Effector Coupler Stem, U.S. Appl. No. 29/721,682, filed Jan. 22, 2020, End Effector Coupler Stem.

U.S. Appl. No. 16/879,500, filed May 20, 2020, End Effector Coupler for Surgical Arm.

U.S. Appl. No. 15/919,150, filed Mar. 12, 2018, End Effector Coupler for Surgical Arm.

U.S. Appl. No. 15/919,161, filed Mar. 12, 2018, End Effector Coupler for Surgical Arm.

\* cited by examiner

RAPIDLY REPOSITIONABLE POWERED SUPPORT ARM

CROSS-REFERENCE TO RELATED APPLICATIONS

This application claims the benefit of the following provisional patent applications: (1) 62/139,535, filed on Mar. 27, 2015; (2) 62/169,440, filed on Jun. 1, 2015; (3) 62/213,509, filed on Sep. 2, 2015; and (4) 62/280,631, filed on Jan. 19, 2016. The full disclosures of each of these prior provisional applications is incorporated herein by reference.

BACKGROUND OF THE INVENTION

1. Field of the Invention

The present invention relates generally to apparatus and systems for supporting surgical and other tools. In particular, the present invention relates to lockable, articulated arms for supporting surgical and other tools.

In many industrial and medical applications, it is desired to have a repositionable, low-profile arm capable of securing and supporting objects in space. For example, in the field of surgery, it is common for multiple instruments and retractors to be used simultaneously for different purposes including exposure and visualization of the surgical site as well as performing a desired procedure. Since the surgeon can typically hold and manipulate only one instrument in each hand, surgical assistant(s) and/or repositionable support arms are often used to hold additional instruments. Since additional personnel are costly, crowd the operating area, and have difficulty holding instruments steady over long time periods, repositionable support arms are an attractive option.

Most repositionable support arms used in surgery include two or more arm segments held together by joints that are locked and unlocked by the surgeon or assistant using one or more threaded knobs or levers. If the joints are not tightened sufficiently, the instruments can "drift" which at a minimum is an inconvenience and can sometimes present a significant risk to the patient. While simple in theory, in practice it can be difficult to apply the necessary force to the locking knob or lever while simultaneously holding the instrument steady at a desired place and orientation. Another challenge in using conventional repositionable support arms is that two hands are required: one to hold the instrument and another to tighten the knob(s) or lever(s) A third challenge is that the process of unlocking the arm, re-positioning the instrument, and retightening the arm is cumbersome and takes valuable time away from the operation.

To partially address these challenges, repositionable support arms have been proposed that use a push button or switch to control a power supply or stored energy source (e.g. compressed gas) to lock the arm joints. Such arms can be rapidly locked and unlocked, making the instrument repositioning task less cumbersome. To date, however, such powered repositionable support arms have been bulky, expensive, difficult to sterilize, and prone to joint slippage due to low joint locking forces.

Thus, it would be useful to provide repositionable, lockable support arms for surgery and other purposes that offer one or more of rapid adjustability and instrument placement, one-handed operation, high joint locking forces and instrument stability, compact profile, simple sterilization, and low cost. The present invention preferably provides at least some of these objectives.

2. Background Art

Relevant background patents include: U.S. Pat. Nos. 4,402,481; 4,606,522; 6,491,273; 3,910,538; 6,575,653; 3,858,578; and 5,020,933.

SUMMARY OF THE INVENTION

In a first aspect, the present invention provides a lockable, repositionable support assembly comprising a base arm having a lower end and an upper end, a distal an having a proximal end and a distal end, a central joint directly or indirectly linking the upper end of the base arm to the proximal end of the distal arm, a lower joint at the lower end of the base arm, an upper joint at the distal end of the distal arm, and a locking mechanism (typically including an actuator as described below) coupled to the base arm at a location above the lower joint and configured to simultaneously deliver locking forces to the lower joint, to the center joint, and to the upper joint. By "above," it is meant that the locking mechanism is on a side of the lower joint which is distal the lower joint, i.e. in the direction toward the center joint. The lower joint of the lockable support assembly will typically be configured to be removably attached to a surface such as a side rail on a surgical bed, often indirectly by a pole or other intermediate support element. The upper joint will typically be configured to removably attach a tool or tool holder for surgery or other purposes.

The joints may have any configuration of a type used in lockable, repositionable support assemblies, typically being spherical or ball joints which provide a "universal" pivoting motion in three-dimension space, rotational joints which provide rotation in a plane relative to an axis, translational joints which allow movement along a straight, curved or other line, and the like. In the specific embodiments, the central joint is usually a rotational joint while the upper and lower joints are typically spherical joints.

The locking mechanism of the present invention may also have a variety of configurations. Suitable locking mechanisms will typically deliver locking forces by at least one of compression (e.g. pushing), tension (e.g. pulling), rotation, or combinations thereof. The locking forces will engage or interact with the joints to selectively immobilize the joints which in turn will hold or lock the joints and arms in a desired position. When the joints are free of locking forces, the joints and arms will be manually repositionable so that a user can place a tool, instrument or other article held at the distal end of the distal arm in a desired location and orientation, and after the position is satisfactory, apply the locking force to immobilize the arm and hold the tool or instrument in place until the arm is released.

In specific embodiments, the locking mechanism comprises a "powered" bilateral force generator which transmits a locking force in one axial direction to the lower joint and in an opposite axial direction to the central joint and the upper joint. The locking mechanism will usually comprise an upper base rod which transmits the locking force from one side of the bilateral force generator to the central joint and a distal rod which transmits the locking force from the central joint to the upper joint. The locking mechanism may further comprise a lower base rod or extender which transmits force from an opposite side of the bilateral force generator to the lower joint. Alternatively, the lower ball joint may be coupled directly to the opposite side of the bidirectional force generator. In the illustrated embodiments, the bilateral force generation may be fluidically powered, e.g. hydraulically and/or pneumatically, or may be electrically powered.

The term "rod," as used herein, includes any elongate structure or member having an axis and being capable of transmitting mechanical force via compression (e.g. pushing in the axial direction), tension (e.g. pulling in the axial direction), and/or rotation about the axis. The rod is illustrated as a simple cylindrical elongate element, but may have other geometries, such as beams having rectangular or other non-circular cross sections, and the like. The rods will usually be formed in one piece but could also be formed with two or more segments joined together to transmit the desired force. Usually, the rods will be rigid but in some cases could be non-rigid, e.g. when used for applying tension between joints or other elements.

In fluidic embodiments, the bilateral force generator comprises a hydraulic or pneumatic driver with a piston which travels in a first axial direction and a cylinder or a second piston which travels in a second axial direction. The driver is axially aligned with the base arm so that the piston is disposed to transmit locking force in one axial direction along the base arm, e.g. to the central joint, and the cylinder or second piston is disposed to transmit locking force in the other axial direction, e.g. to the lower joint. The fluidic bilateral force generators will usually also include a fluidic generator, e.g. a generator which produces pressurized hydraulic or pneumatic fluid. The fluidic generator will typically be located remotely from the hydraulic or pneumatic driver and will be connected to the driver by fluidic connecting lines.

In electrically powered embodiments, the bilateral force generator may comprise an electric motor and a force multiplier means. The multiplier means may comprise a lead screw driven by a motor and a follower which travels over the screw. Alternatively, the multiplier means may comprise a mechanical linkage consisting including two links coupled together with three pin attached in-line with the upper base rod. Other multiplier means include a combination of a gear reduction, a screw drive, a rack-and-pinion drive, or a roller-wedge mechanism.

In other specific embodiments, the central joint comprises a rotational joint having an axle joining the upper end of the base arm to the proximal end of the distal arm and wherein an interface surface at the upper end of the base arm frictionally engages an interface surface on the proximal end of the distal arm such that the locking mechanism drives the interface surfaces together to prevent relative movement of the arms. Such rotational joints may further comprises a first inclined surface which receives force from the upper base rod and a second inclined surface which transmits force to the distal rod, wherein the aligned surfaces are coupled by the axle which both (1) locks the interface surfaces together; and (2) translates the second inclined surface in response to the upper base rod engaging the first inclined surface. The upper and lower joints may each comprise spherical joints including a friction block which is coupled to the bilateral force generator to lock the spherical joint when the generator generates a locking force or is otherwise actuated.

The lockable, repositionable support assemblies of the present invention also allow for convenient draping, sterilization, and replacement of the sterilized components. In particular, the lockable support assemblies of the present invention may comprise a base arm which is separable from the locking mechanism to allow removal of the base arm, distal arm, and central and upper joints to permit sterilization or replacement of the base arm, distal arm, and central and upper joints.

A lockable support system may comprise the lockable support with a sterile drape configured to cover the locking mechanism when the base arm, distal arm, and joints are connected to the locking mechanism.

In a second aspect, the present invention provides a lockable support assembly comprising a base arm having a lower end and an upper end, a distal arm having a proximal end and a distal end, a center joint directly or indirectly linking the upper end of the base arm to the proximal end of the distal arm, a lower joint at the lower end of the base arm, an upper joint at the distal end of the distal arm, a powered locking mechanism configured to simultaneously engage the lower joint, the center joint, and the upper joint to deliver locking forces to said joints to prevent relative motion of said arms, and a latching mechanism which prevents the arms from moving and/or prevents the locking mechanism from disengaging the joints upon loss of power to the locking mechanism.

The locking mechanism typically comprises a force generator which transmits a locking force through the base arm and the distal arm to lock the joints, and the force generator usually comprises a fluidic driver, e.g. hydraulic or pneumatic, with at least a first piston which travels in a first direction and a second piston or cylinder which travels in an opposite direction to transmit the locking force. Alternatively, the force generator may comprises a motor which is coupled by a force multiplier to deliver forces to the center, lower and upper joints.

The latching mechanism may comprise a spring-loaded element which is constrained while the assembly is receiving power and which is released from constraint to latch the locking mechanism and/or arms when power is lost. Alternately, the latching function may be provided by the non-reversible nature of the force multiplier.

In a third aspect, the present invention provides a lockable support assembly comprising a base arm having a lower end and an upper end, a distal arm having a proximal end and a distal end, a center joint directly or indirectly linking the upper end of the base arm to the proximal end of the distal arm, a lower joint at the lower end of the base arm, an upper joint at the distal end of the distal arm, a powered locking mechanism configured to simultaneously engage the lower joint, the center joint, and the upper joint to deliver locking forces to said joints to prevent relative motion of said arms, wherein the arms remain locked when the powered locking mechanism loses power; and an override mechanism to permit manual repositioning of the arms upon loss of power to the locking mechanism.

The override mechanism temporarily disengages the locking mechanism to permit manual repositioning and relocking of the arms when the powered locking mechanism loses power. The force generator may comprise a hydraulic or pneumatic cylinder with at least a first piston and a second piston or a cylinder which travel in opposite directions to transmit the locking force. The force generator may comprise a motor which is coupled by a force multiplier to deliver forces to the center, lower and upper joints, wherein the override mechanism disengages the lead screw.

In a fourth aspect, the present invention provides a lockable support assembly comprising a base arm having a lower end and an upper end, a distal arm having a proximal end and a distal end, a center joint directly or indirectly linking the upper end of the base arm to the proximal end of the distal arm, a lower joint at the lower end of the base arm, an upper joint at the distal end of the distal arm, and a powered locking mechanism configured to simultaneously engage the lower joint, the center joint, and the upper joint to deliver locking forces to said joints to prevent relative motion of said arms, wherein at least some of the joints are biased to eliminate or reduce clearances in the joint or locking mechanism in the absence in the absence of locking forces to prevent an unintended change of arm position when as the locking mechanism engages the joints.

The locking mechanism may comprise a force generator which transmits a locking force through the base arm and the distal arm to lock the joints, and the force generator may comprise a fluidic (e.g. hydraulic or pneumatic) cylinder with at least a first piston and a second piston or a cylinder which travel in opposite directions to transmit the locking force. Alternatively, force generator may comprise a motor which is coupled by a force multiplier to deliver forces to the center, lower and upper joints.

In another aspect of the present invention, the locking arm assembly may further include a lock/unlock button or switch disposed near a distal end of the distal arm to enable one-handed instrument manipulation and unlocking/locking. The lock/unlock button or switch may be configured to initiate or enable operation of the any of the locking mechanism described and claimed herein.

In still another aspect of the present invention, locking forces may be transmitted substantially simultaneously to the lower joint, center joint and upper joint using mechanical elements.

In yet another aspect of the present invention, the base, the distal arm, the central joint, the lower joint, and the upper joint are configured to be driven solely by the locking mechanism and the locking mechanism is powered by a single connector. This is advantageous as the lockable support assembly does not have to interface with other power sources external to the assembly. Elimination of such interfaces is beneficial to improve clinical workflow, and is made possible by the efficient power utilization of the lockable arm of the present invention.

BRIEF DESCRIPTION OF THE DRAWINGS

FIG. 6a-6h are detailed cross-sectional views of the central rotational joint of FIGS. 1-4.

FIG. 22a is a perspective view and FIG. 22b is a cross-sectional view.

FIGS. 25a-f show preloading embodiments with a spring located at the center rotational joint, and FIGS. 25g-h show preloading embodiments with a spring located at the base spherical joint and/or distal spherical joint.

FIG. 27a shows a 3D view and FIG. 27b shows a cross-sectional view.

DETAILED DESCRIPTION OF THE INVENTION

Figure 1:
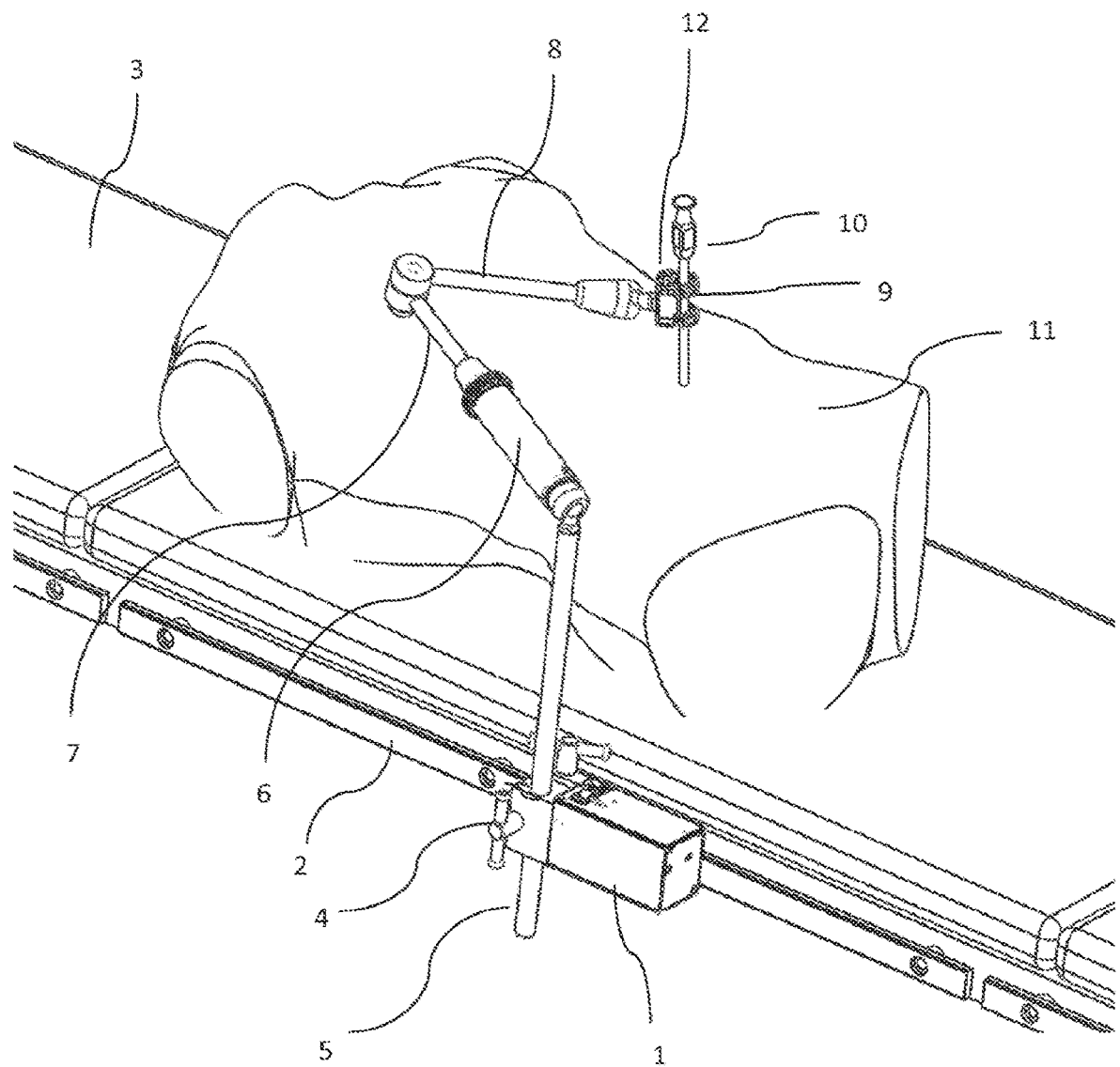
FIG. 1 shows a repositionable, lockable support arm constructed in accordance with the principles of the present invention incorporating an electric locking mechanism.
Figure 2:
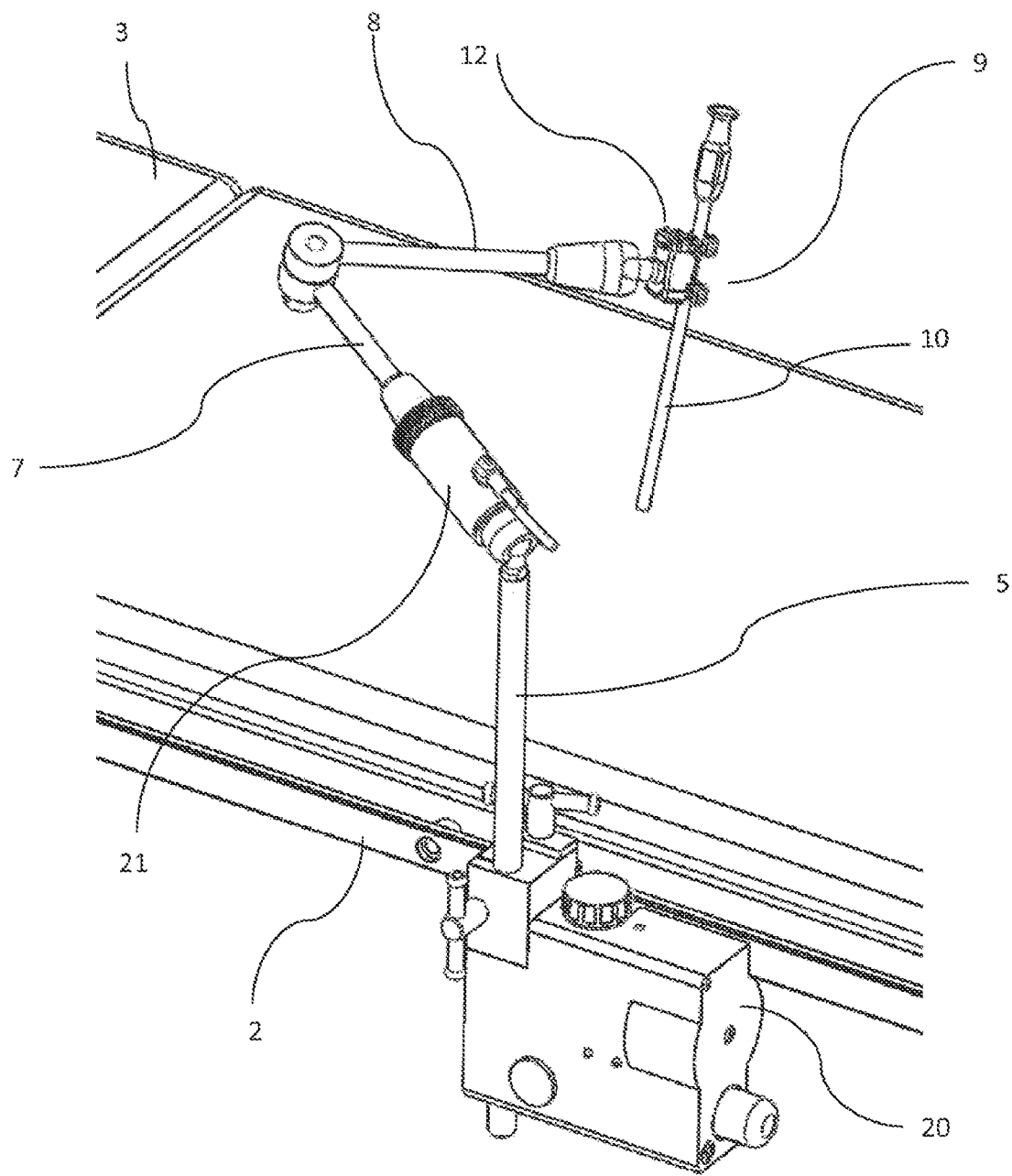
FIG. 2 shows a repositionable, lockable support arm constructed in accordance with the principles of the present invention incorporating a fluid powered locking mechanism.

FIG. 1 shows a repositionable, lockable support arm constructed in accordance with the principles of the present invention in use in a surgical procedure on a patient (11). An electric base unit (1) clamps to the railing (2) of a surgical table (3). A manual clamp (4) on the base unit tightens the base unit (1) against the railing (2) and enables adjustment of a pole (5) that determines the height of the arm above the surgical table. The arm itself consists of an electric actuator unit (6) near the proximal base, a base arm segment (7), and a distal arm segment (8). An instrument holder (9) connects an instrument (10) to the distal end of the arm. A lock/unlock button (12) is provided on or near the instrument holder so that a user can initiate power locking and unlocking of the arm with the same hand that positions and/or holds the instrument at a desired location and orientation relative to the patient (11). In FIG. 1, the joints are locked and unlocked with an electric base unit (1) and an electric bilateral actuator (6), as further described with reference to FIG. 7 below. In FIG. 2, the joints of the arm are locked and unlocked with a fluid system consisting of a fluid base unit (20) and a fluid bilateral actuator (21), as further described with reference to FIGS. 8-10 below.

The locking arms of FIG. 1 and FIG. 2 comprise a serial linkage of arm segments joined by spherical and rotational joints. As shown in more detail in FIG. 3, the base arm segment (7) and distal arm segment (8) are connected with a central rotational joint (30). A base spherical joint (31) is held in a base sphere retainer (35) located at a proximal or "base" end of the actuator unit (400) which is connected to a proximal end of the base arm segment (7). A distal spherical joint (32) is held in a distal sphere retainer (36) located at the distal end of the distal arm segment (8). An additional distal rotational joint (33) may be provided between the distal spherical joint (32) and central rotational joint (30) to permit rotation of the distal sphere retainer (36) with respect to the distal arm segment (8). Similarly, a rotatable base joint (34) may be provided between the proximal end of the base arm segment (7) and the actuator (400) to enable rotation of the base arm segment (7) with respect to the base sphere retainer (35). In some preferred embodiments the spherical retainers have a slot (37) which allows for extended pivoting of the spherical joint in the slot.

Figure 3:
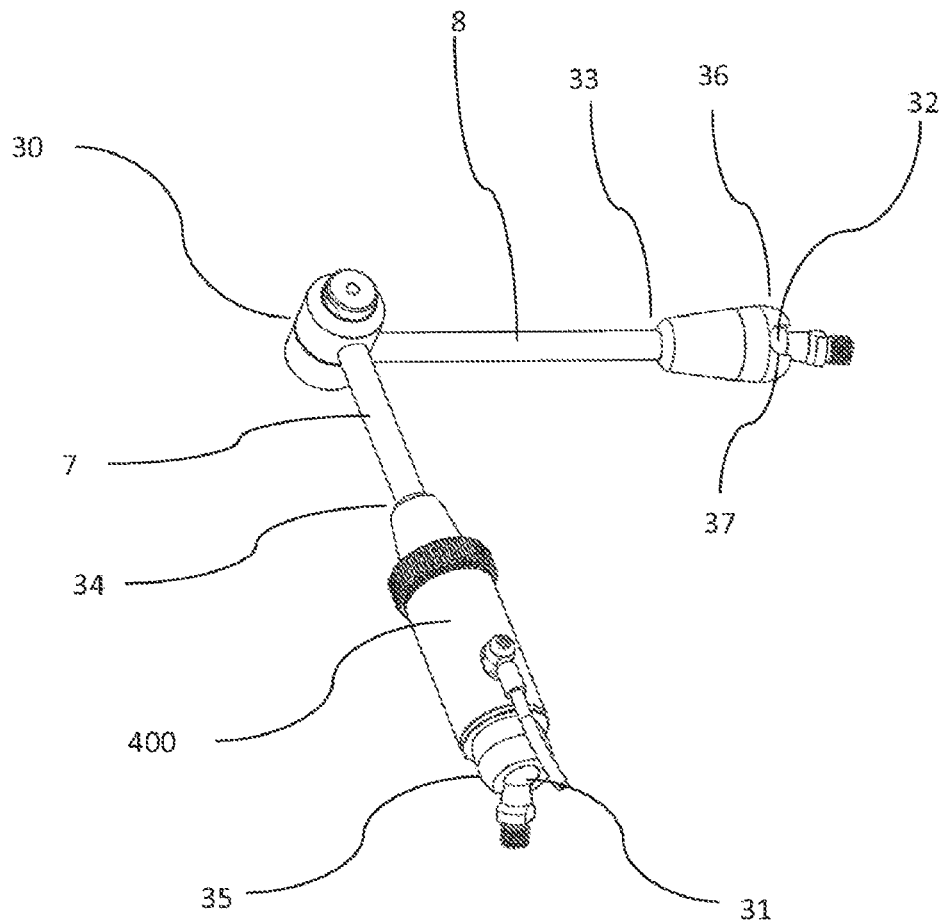
FIG. 3 is an enlarged view of the components in a portion of FIG. 2.

While only base and distal arm segments are illustrated in FIGS. 1-3, additional "intermediate" arm segments could be provided between the central rotational joint (30) and the distal sphere retainer (36) so that the central rotational joint links the upper end of the base arm to the proximal end of the distal arm "directly or indirectly." Each additional arm segment would usually require at least one additional joint, usually one additional rotational joint, to be added to form a repositionable, lockable support arm structure. Such additional arm segments can provide greater coverage and ability for the arm be positioned with more degrees of freedom in the surgical field.

Figure 4:
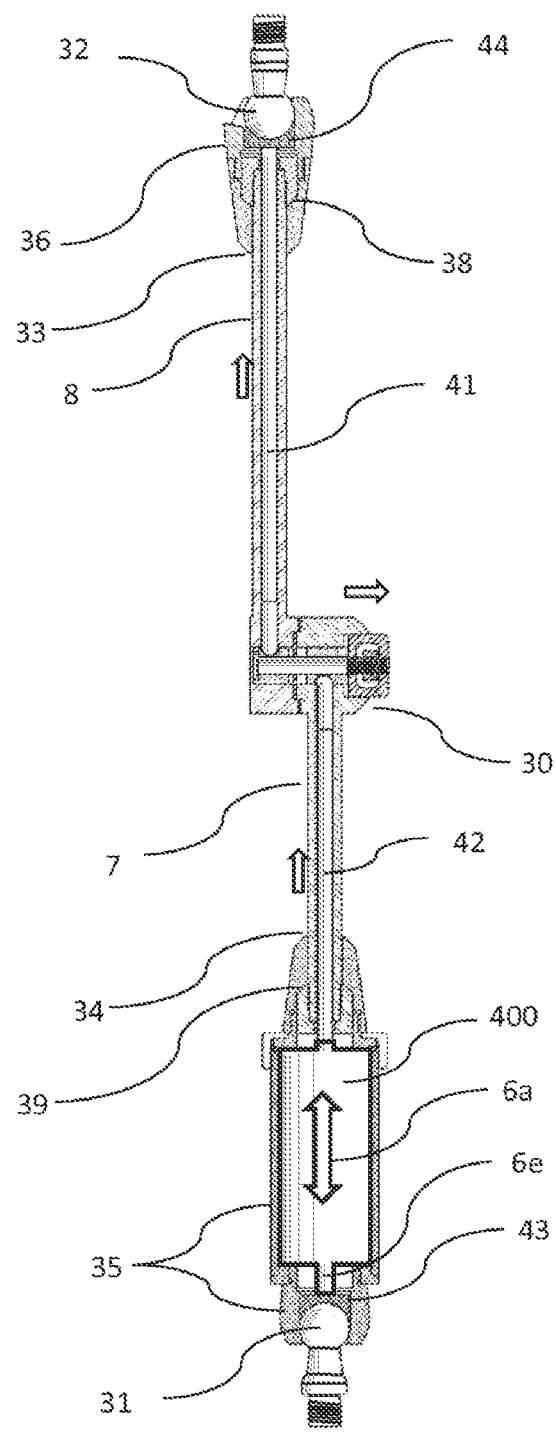
FIG. 4 is a cross-sectional view of the components of FIG. 3.
Figure 5:
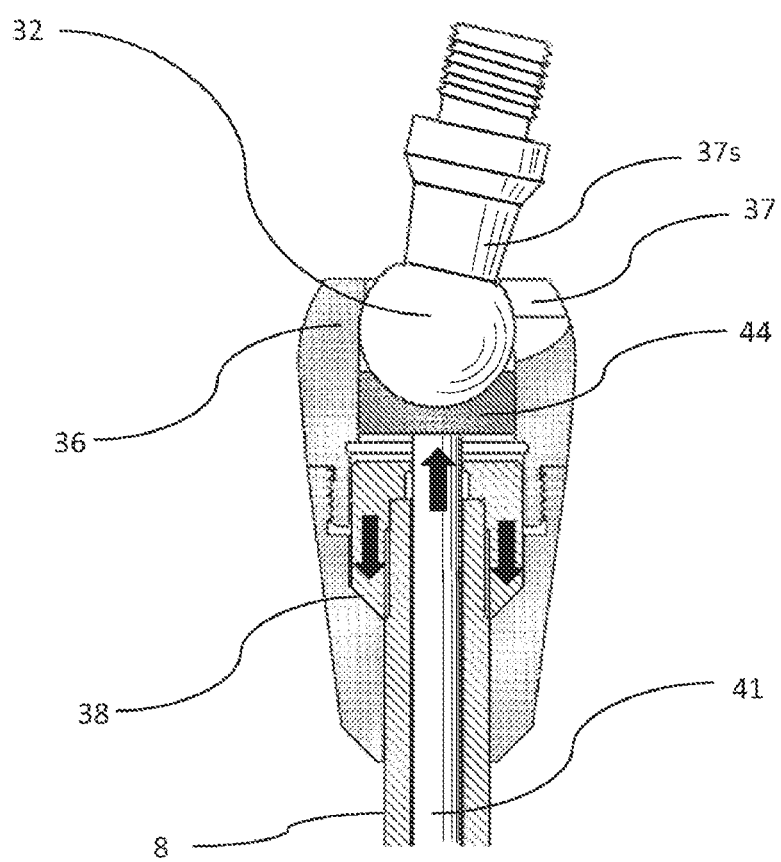
FIG. 5 is a detailed cross-sectional view of a distal joint on a distal end of a distal arm of FIGS. 1-4.

Referring now in particular to FIG. 4 and FIG. 5, locking forces are transmitted "bi-laterally" in proximal and distal directions from the bilateral actuator (400) as indicated by arrow (6a). A distal rod (41) and an upper base rod (42) extend through axial passages in the base arm segment (7) and the distal arm segment (8), respectively, and transmit the locking forces in a distal direction to the central rotational joint (30) and the distal spherical joint (32). A proximal force from the actuator (400) is transmitted by an extender (6e) at a proximal or base end of the actuator (400) to lock the base. Compressive loads on the distal rod (41), the upper base rod (42) and extender (6e) push on the spherical joint friction blocks (43) (44) which apply pressure to both spherical joints (31) and (32) substantially simultaneously. The compressive loads on the extender (6e) result from expansion of the actuator (400) which is in contact with the extender. The compressive loads on the inner rods cause reaction forces (extensive loads) through the base and distal arm segments (7) (8). These reaction forces are transmitted through a base and distal ramped interface (39) (38) between the arm segments (7) (8) and the sphere retainers (35) (36), thus applying frictional forces at the ramped interface and locking the base and distal rotational joints (34) (33). While FIG. 5 shows the distal or upper spherical joint (32), the details are similar for the base spherical joint (31).

Figure 6A:
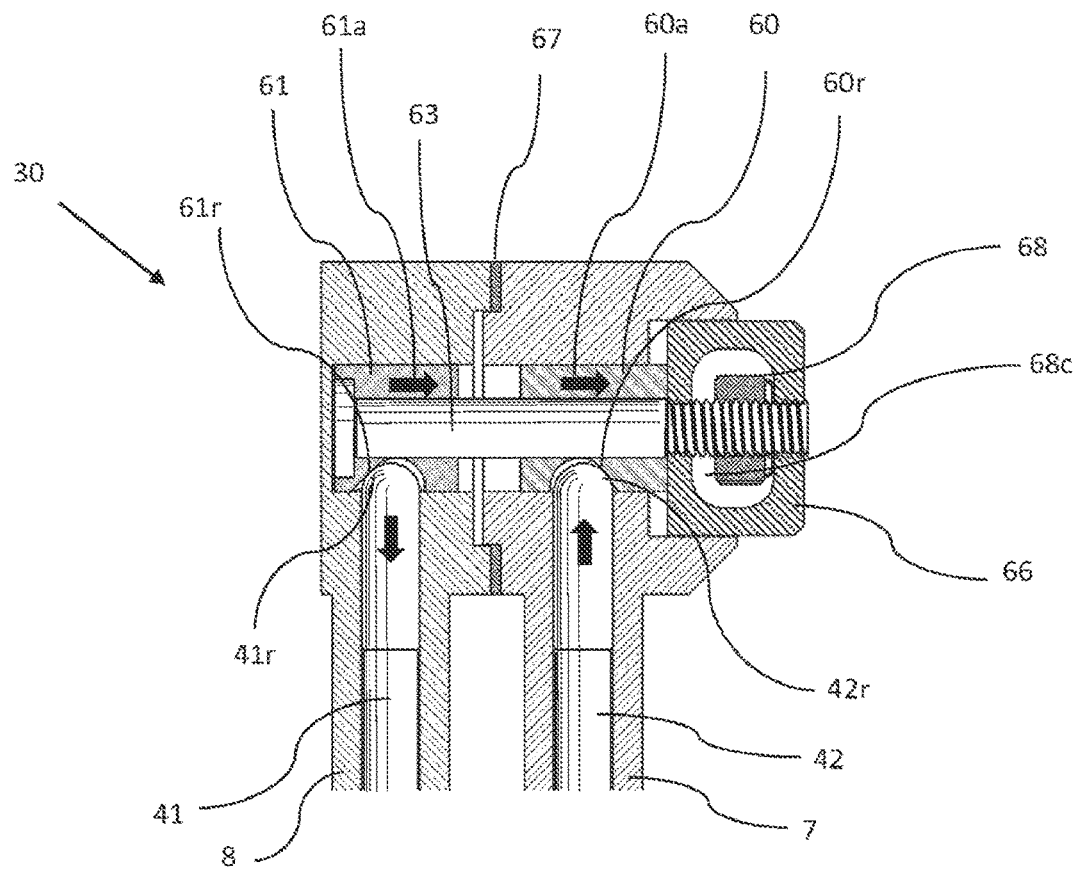
Figure 6B:
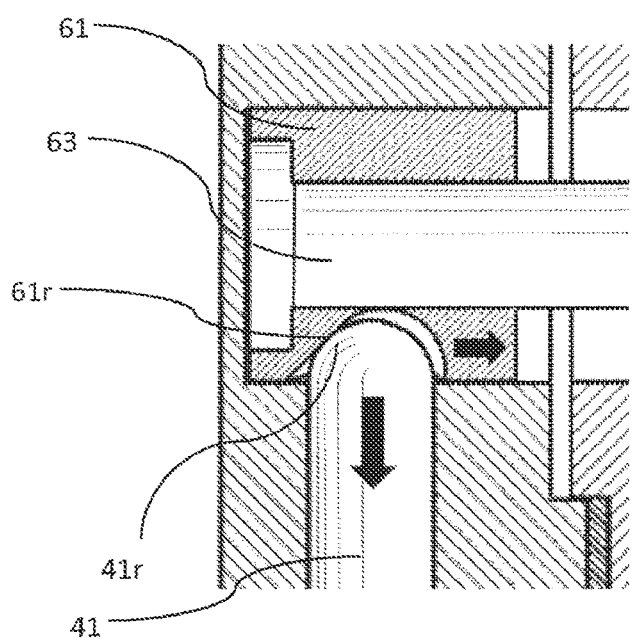

FIG. 6a shows the center joint (30) in more detail and illustrates how locking forces are transmitted from the upper base rod (42) in the base arm segment (7) to the distal inner rod (41) in the distal arm segment (8). The center joint (30) defines a motion/force transfer mechanism that receives a locking force from the upper base rod (42) and simultaneously applies the locking force to the center joint itself and to the distal rod (41). This transfer mechanism includes a base slug (60) and distal slug (61). A ramp interface (42r) on the distal end of the upper base rod (42) pushes against a ramp interface surface (60r) on the base slug member (60) as the upper base rod (42) is pushed upward by the actuator (400) (FIG. 4). The angle of the ramp interface surface (60r) causes the base slug (60) to translate laterally away from the base side of the arm in the direction of arrow (60a). A capped axle member (63) connecting the base slug (60) and distal slug (61) causes the distal slug (61) to translate medially towards the base side of the arm in the direction of arrow (61a). As the distal slug (61) translates medially, a distal ramp interface (61r) engages a ramp interface (41r) on the distal rod (41) to push the rod in the direction of the distal spherical joint (32). A distal end of the distal rod (41) pushes the friction block against the ball of the distal spherical joint (32), locking the distal spherical joint (32) in place. FIG. 6b is a detailed cross sectional view of the distal ramp interface.

Referring back to FIG. 6a, when the distal slug (61) translates medially, the distal ramp interface (61r) causes a medially-directed force to be applied between the distal inner rod (41) and the distal arm segment (8). This force causes the entire distal half of the arm to exert a force on the base half of the arm at the central rotational joint interface, thus applying a locking force to the central rotational joint (30). A friction washer (67) at the central rotational joint increases the central rotational joint locking torque. Note that, by design, the system has small clearances between moving parts. As a result, only a small magnitude of motion (typically less than 2 mm) of the actuator can move the system between the locked and released state.

Another feature depicted in FIG. 6a is a manual lock and unlock backup or override mechanism for use in case of actuator failure. A threaded knob (66) is placed over a threaded shank of the axle member (63). The knob can be turned to increase or decrease a locking force on the base slug (60) and distal slug (61) which in turn tightens or expands the center joint, thus manually locking or unlocking the entire arm independent of the state of the actuator. Such manual locking features could be placed anywhere along any of the members in the clamping path (refer forward to FIG. 26). Axle member (63) may have a key restricting its rotation relative to the base slug (60). In the embodiment shown a locking nut (68) is affixed onto the axle. The axial clearance (68c) between the knob (66) and the nut (68) provides a limited range of motion of the knob. This motion may correspond to the actuation range ensuring that the joints are not too loose nor may not be over tightened. In another embodiment, instead of a knob (66), there may be an interface that requires a tool to operate. This prevents accidental operation of the knob.

Actuators of many sorts are known to one skilled in the art. In a preferred embodiment of the invention, the actuator (400) has the property of being "normally on" That is, if actuator power is lost while the arm is locked during a medical procedure, the arm will remain locked such that the instrument being held does not lose its position. Unexpected unlocking of the an can have serious medical consequences when the instrument being held is in a delicate or sensitive position with respect to the patient (for example, a transnasal endoscope used for visualization during pituitary brain surgery). Therefore in one embodiment of the invention, the actuator is powered electronically with a non-backdrivable force multiplier.

Figure 7:
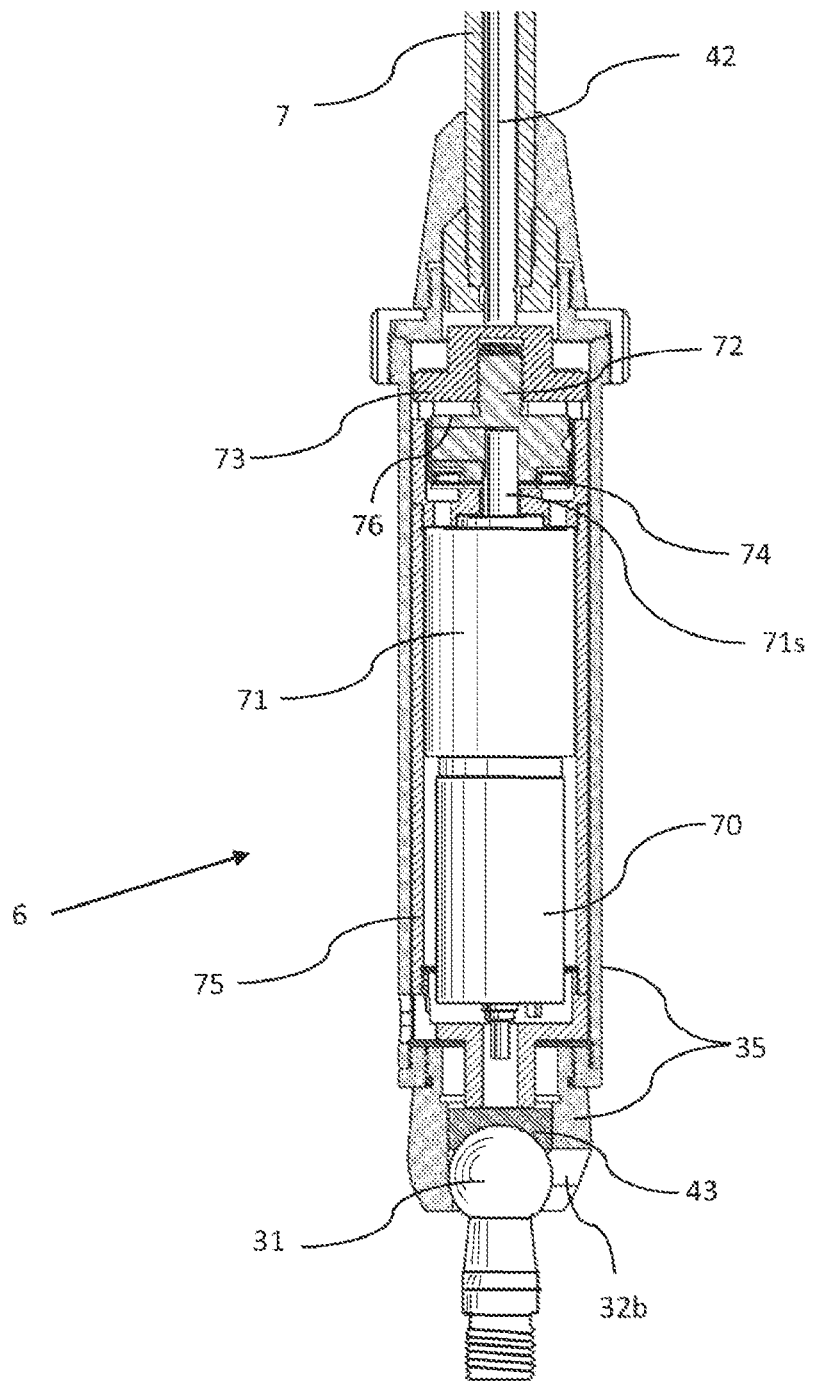
FIG. 7 is a detailed cross-sectional view of the electric locking mechanism of FIG. 1.
Figure 8:
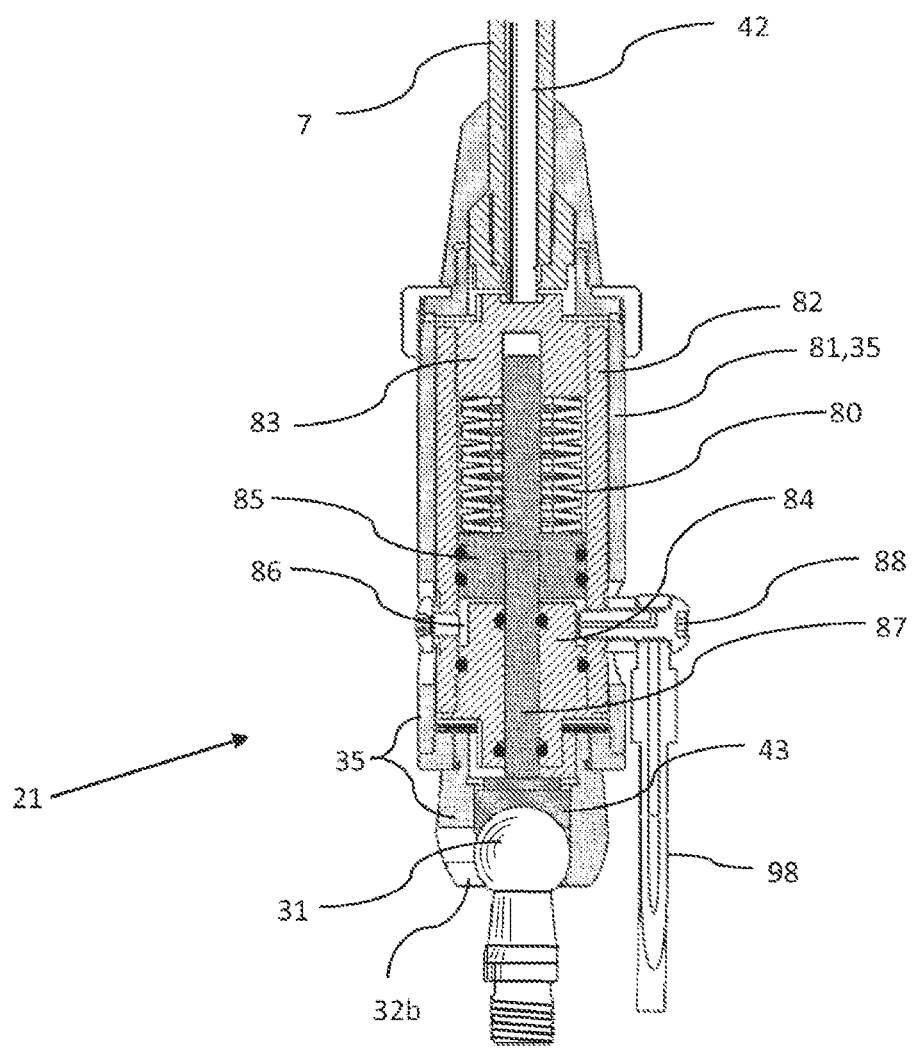
FIG. 8 is a detailed cross-sectional view of the fluid locking mechanism of FIG. 2.

Referring to FIG. 7, an electric bilateral actuator (6) generally comprises a lead or drive screw driven by a motor and a nut or other follower which travels over the screw. A specific embodiment is shown in cross section. A motor (70) with planetary gearhead (71) turns a gearbox shaft (71s) coupler rigidly attached to a lead screw body (72). Rotation of the lead screw causes a lead nut (73) to translate with respect to the shaft assembly, compressing the upper base rod (42) and motor cage (75). Flanges (not shown) on the lead nut and motor mount constrain motion to pure translation and prevent the lead nut from rotating with respect to the assembly. A thrust bearing (74) supports the large compressive loads. The motor transmission design (gearbox and lead screw) can be selected to prevent "back driving" of the gears which is advantageous because the actuator will remain in its current state in the event of a power or motor failure, and thus the arm remains in its current state (locked or unlocked). In alternate embodiments, the lead screw may be replaced with alternate multiplier means may include a combination of a gear reduction, a differential screw drive, a rack-and-pinion drive, worm gear drive, a roller-wedge mechanism, roller ball mechanism (FIG. 14), or other means.

To drive the system and lock with a particular force, a particular torque must be applied to the motor. Since current is proportional to torque, by precisely limiting the maximum current during the locking phase, a particular joint locking force can be achieved. Since maximum current can be software-selectable using a current sensor, the locking force can be software-selectable in this embodiment. Current can be conveniently drawn from a battery that is located in the base unit of the arm (1), thus making the system a self-contained unit and eliminating the need to plug in external cords.

When the nut (73) is returning to its "home" proximal position (76), a contact switch (not shown) can be used to shut the motor off before it hits the "hard stop" at its home position, thus preventing motor damage and limiting "shock loads" on the system. In another embodiment, a stiff "crash spring" (not shown) can be provided at the home position (76). This spring may be a rubber disk, ceramic brake disk, Belleville disk spring, or other material.

In another embodiment of the invention, the bilateral actuator is powered with fluid (preferably hydraulic fluid). This is depicted in cross section in FIG. 8. The actuator includes an outer case (81) which is rigidly connected to the base sphere retainer. Inside this case is the actuator cylinder body (82) that is free to move axially inside the case. The actuator body is rigidly capped at the ends by an upper cap (83) and lower cap (84). Disposed inside the actuator body is a piston (85) which is rigidly fixed to a piston extender rod (87). The volume between the bottom of the piston (85) and the top of the lower cap (84) forms a small hydraulic void (86). When fluid is pumped through a hose (98) to the hydraulic fittings (88) and into this void, the piston extender rod (87) retracts towards the actuator body (82). This removes the force from the friction block (43) releasing the base spherical joint. In a preferred embodiment this small motion also releases the entire arm linkage chain. The hydraulic force acts against a stiff stack of springs (80). The stack is preferably stiff enough that the assemblage acts like a rigid compressive element in the normally locked linkage. This embodiment has the advantage of not unlocking the system when the actuator becomes inactive due to loss of fluid pressure, loss of power, or other compromised scenarios.

Figure 9:
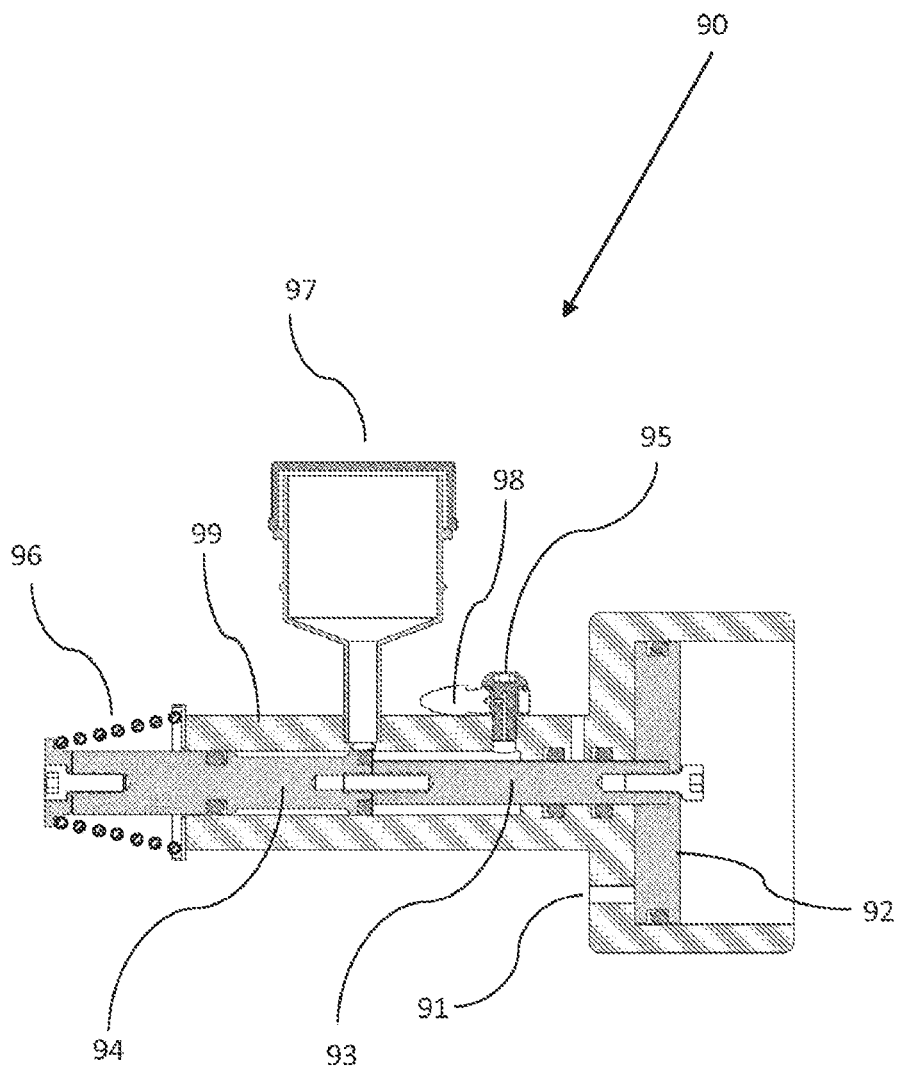
FIG. 9 shows a cross-sectional view of a master fluid cylinder assembly that drives the fluid locking mechanism of FIG. 8.

The pressure to actuate the fluid actuator (21) is produced by a fluid base unit (20). Contained within the base unit (20) is a master cylinder assembly (90). A cross-sectional view of the master cylinder assembly is shown in FIG. 9. Pressurized gas enters into a port (91) in the outer cylinder casing (99) and pushes on a gas piston (92). The force on the piston is transferred through the connecting rod (93) to the hydraulic piston (94). Displacement of the hydraulic piston pumps hydraulic fluid out of the hydraulic fittings (95) which connect via hose (98) to the slave fittings (88) shown in FIG. 8.

When the gas pressure is relieved, a spring (96) connected between the rigid piston assembly and the outer cylinder casing (99) returns the gas and hydraulic pistons to their base position. A fluid reservoir (97) supplies additional hydraulic fluid to the system as needed. The hydraulic piston (94) generally has a smaller active area than the pneumatic piston (92) to create much higher pressures in the hydraulic line compared to the pneumatic supply pressure. The hydraulic master piston (94) generally has a smaller active area than the hydraulic slave piston (85) to realize greater forces in the slave actuation system versus the master system.

Figure 10:
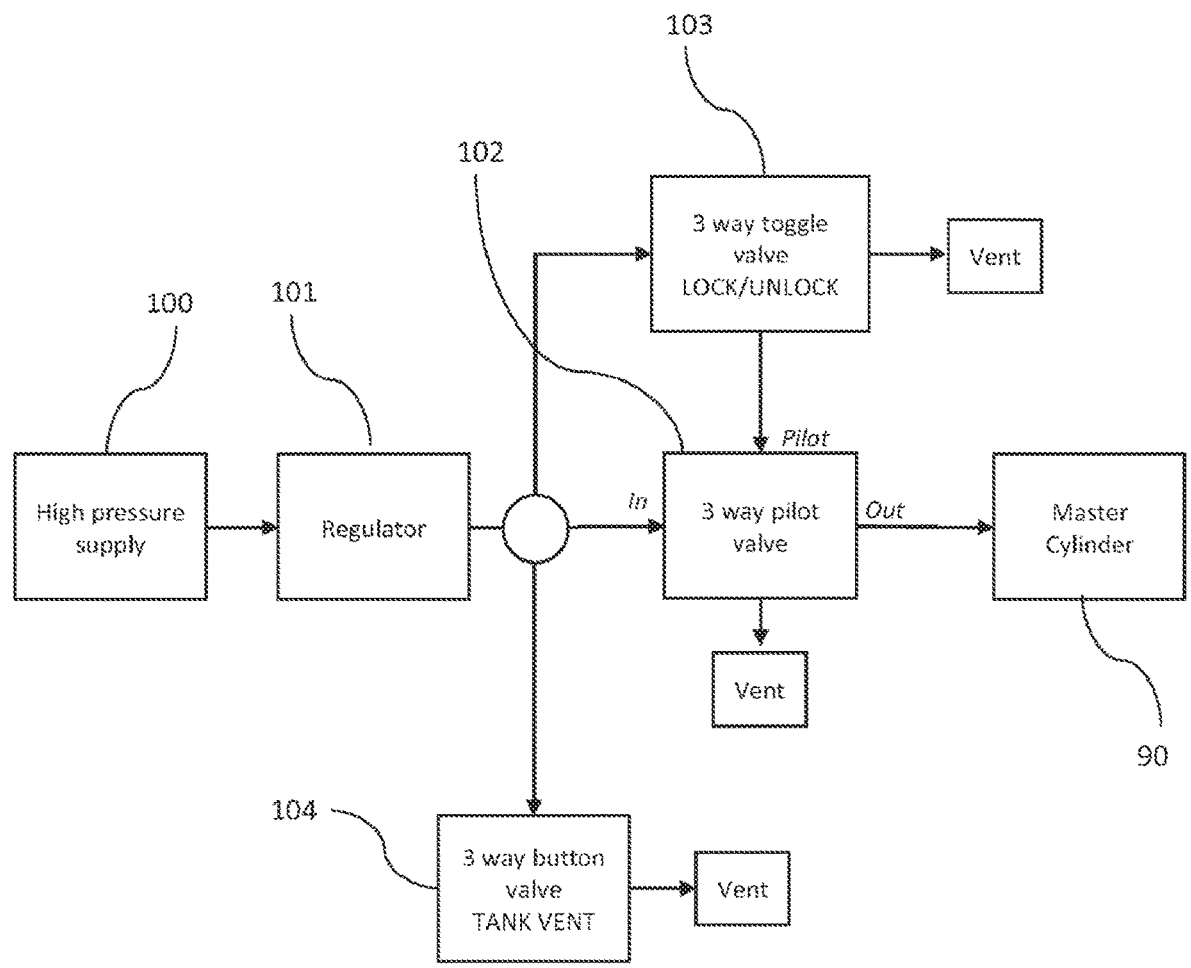
FIG. 10 shows a schematic of a pneumatic system that provides power to the master fluid cylinder assembly of FIG. 9.

To control the gas pressure supplied to the master cylinder assembly (90), the pneumatic system shown schematically in FIG. 10 is used. In a preferred embodiment a high pressure is provided by a miniature gas canister (for example, $CO_2$) that attaches directly to the arm base unit (20). In this manner, the unit is self-contained and does not require any external plugs. In an alternative embodiment, the high pressure supply can come from an external pressure source (for instance, compressed air or nitrogen in an operating room). In either case, the high pressure supply (100) is regulated down to a fixed pressure with a pressure regulator (101). The regulator feeds a 3-way pilot-driven valve (102) that alternatively supplies pressurized air to the master cylinder (90) or vents the master cylinder. The 3-way pilot-driven valve (102) is controlled with a 3-way toggle or push button valve (103) that supplies the pilot with either high pressure air from the regulator (101), or vents the pilot to the atmosphere. The 3-way toggle or push button valve (103) is responsible for determining whether the arm is locked or unlocked, so it is preferably placed near the end effector (distal end) of the arm to enable one-handed instrument repositioning. A final 3-way valve (104) is used to vent the high pressure supply (100) through the regulator (101). This is useful particularly if the high pressure supply is a miniaturized cylinder, enabling the cylinder contents to be quickly vented prior to cylinder removal.

As will be clear to those versed in the art, the hydraulic master cylinder (94) can be actuated by means other than a pneumatic cylinder. For example, the master cylinder can be actuated instead using an electric motor. The motor can be coupled to a mechanical force multiplier system such as a lead screw, eccentric hub, and/or lever to actuate the master hydraulic cylinder (94).

Figure 11:
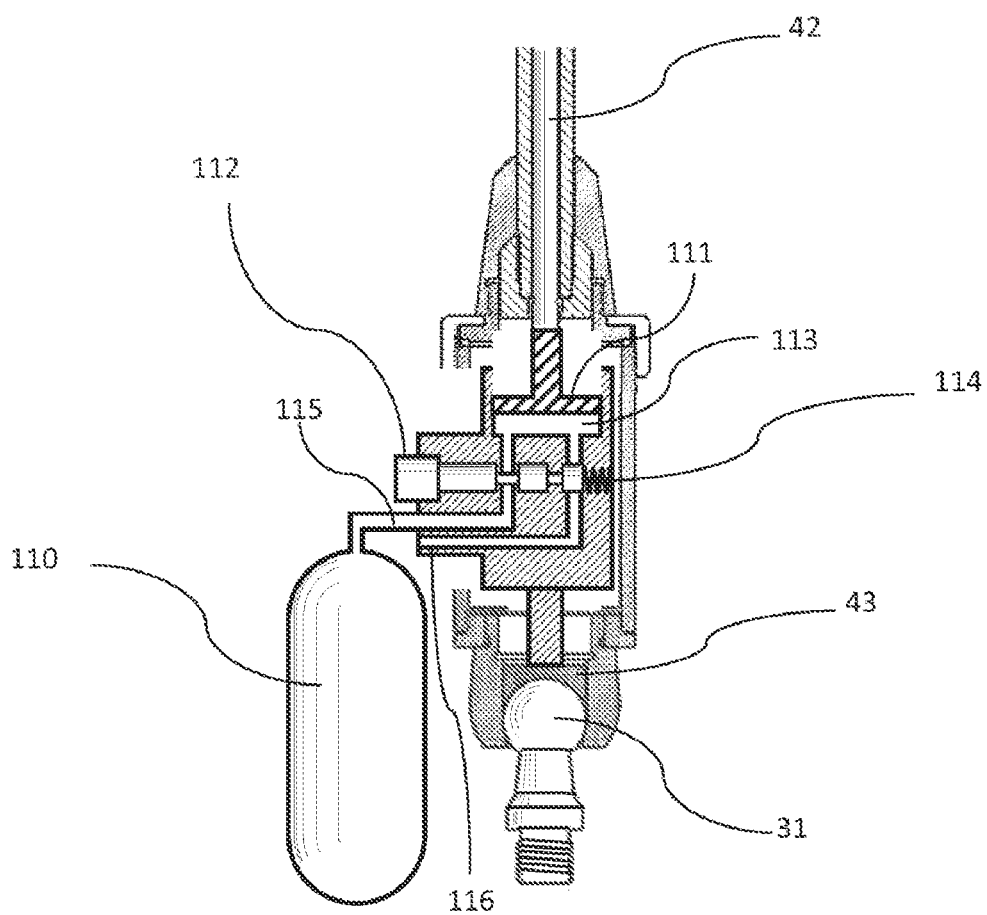
FIG. 11 shows a cross-sectional view of an alternate bilateral locking mechanism embodiment powered directly by pressurized fluid with activation valve adjacent to the fluid piston.

In another embodiment, a bilateral actuator can operate directly using high pressure gas such as CO2 as depicted in cross-section in FIG. 11. For example, a pressurized liquid CO2 canister (110) has a vapor pressure of approximately 850 psi which can provide high force when vented to a gas piston (111). In a simple embodiment, the canister(s) can be attached directly to the arm, close to the actuator. A push button 'Y' valve (112) controls the flow of gas from the attached canister. When the 'Y' valve is depressed, the cylinder chamber (113) vents to the atmosphere through an exhaust port (116), the canister inlet (115) is blocked, and there is no pressure exerted on the piston (111). In this position, the actuator applies no force to the upper base rod (42) or base friction block (43) and the arm joints are unlocked. When the 'Y' valve is released, a spring (114) automatically returns it to a position such that the vent (116) is blocked and the canister inlet (115) is connected to the cylinder chamber (113). In this position, the pressurized gas exerts force on the piston (111) and expands the actuator against the base friction block (43) and upper base rod (42), causing the arm joints to lock. Note that variations are possible, including embodiments where high-force springs are employed to "reverse" the gas actuator such that gas pressure contracts the actuator instead of expands it (similar to the hydraulic embodiment in FIG. 8).

Figure 12:
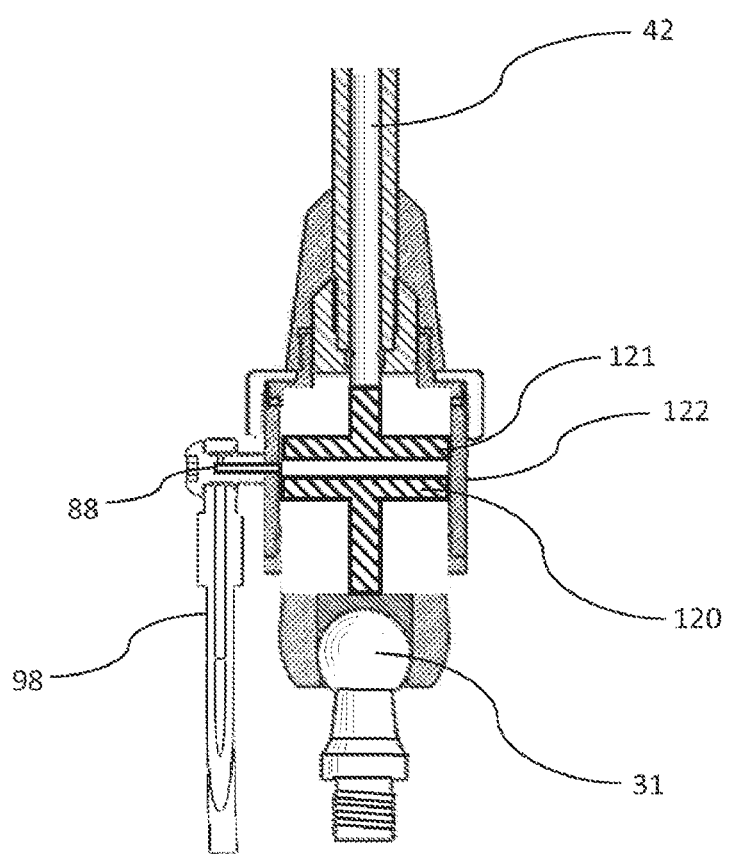
FIG. 12 shows a cross-sectional view of an alternate bilateral locking mechanism embodiment powered by two opposing pistons.
Figure 13:
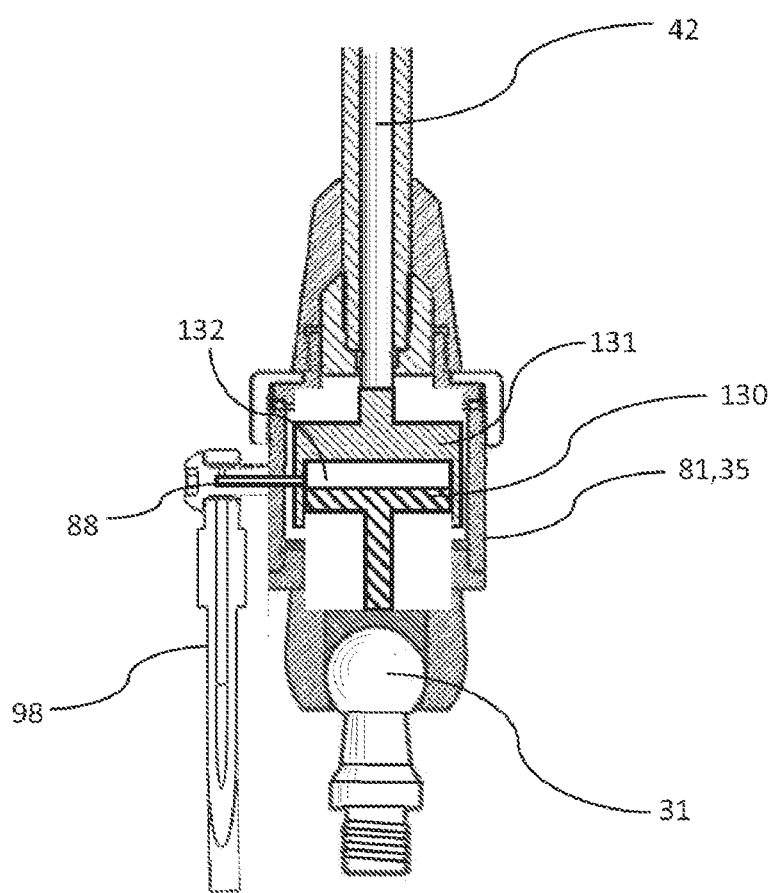
FIG. 13 shows a cross-sectional view of an alternate bilateral locking mechanism embodiment powered by a single piston and movable cylinder.

FIG. 12 and FIG. 13 show other embodiments for the bilateral actuator. In these embodiments, pressurizing hydraulic fluid delivered via hose (98) through hydraulic fittings (88) causes the arm to lock, and depressurizing the fluid results in the arm joints unlocking. In FIG. 12, two pistons (120)(121) actuate in opposite directions relative to a hydraulic cylinder (122) when the cylinder (122) is pressurized. In FIG. 13 a single piston (130) is displaced within a hydraulic cylinder void (132), resulting in expansion of the actuator cylinder body (131) relative to the outer casing (81).

It will be clear to one skilled in the art that a central challenge in the invention is generating sufficient locking force in a short time and releasing it quickly. Great care must be taken in selecting suitable dimensions and specifications for each component so that mechanical stress and strain are within the limits of the materials chosen. The hydraulic and electric solutions are two prominent classes of solutions. There are other potential mechanisms that can be brought to bear to generate the required force in a compact and efficient manner.

Figure 14A:
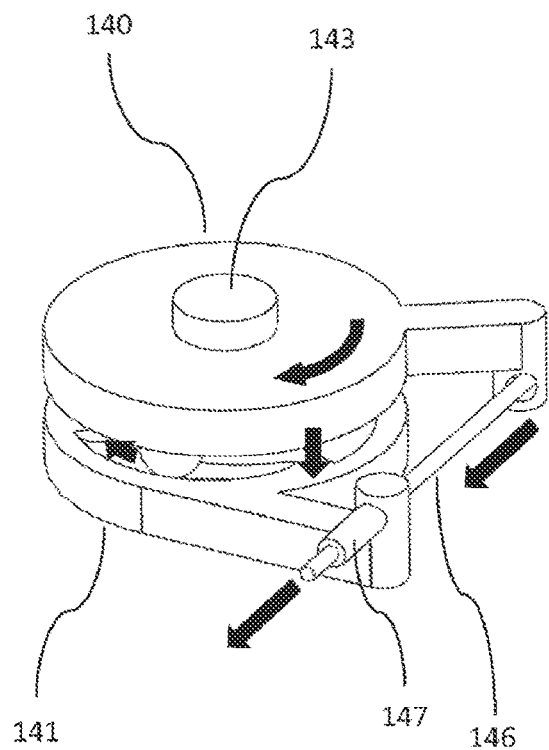
FIGS. 14(a)-(b) show a roller ball joint that provides a mechanical means for forcibly separating two bodies as an alternative to use of pistons in the locking mechanisms of FIG. 8 and FIGS. 11-13.
Figure 14B:
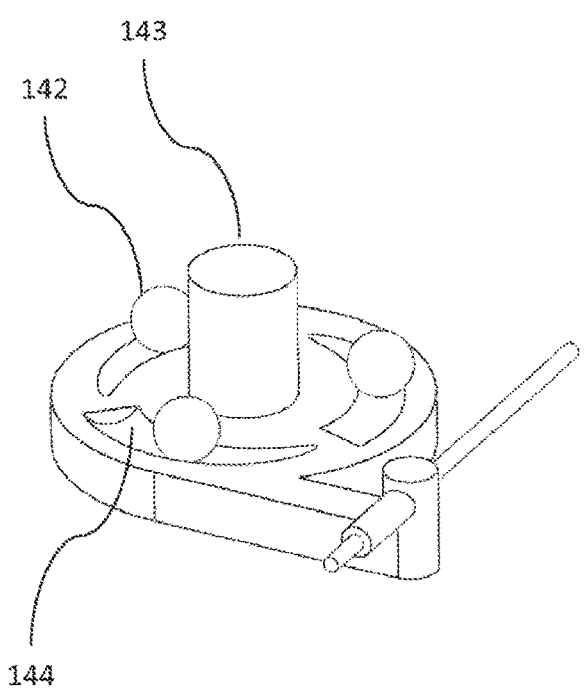

In an alternate set of embodiments, a cable-actuated roller ball disk (FIG. 14a, b) can be used to replace one or more pistons in any of the previously described actuator embodiments. In this setup, two disks (140) and (141) are coupled together using a central shaft (143). FIG. 14a shows the full roller ball disk assembly, and FIG. 14b shows the assembly without the top disk. Each disk has a series of ramped slots (144) (ramp angle θ) that accommodate spherical ball bearings (142). When one disk (140) is rotated relative to the other (141), the balls (142) rotate with respect to the top and bottom ramped slots (144). According to the ramp angle θ, the disk separate apart along the central shaft (143) as a function of the relative disk rotation. The disks may be rotated relative to each other using a mechanical cable (146) which is pulled (e.g. translates) with respect to an outer cable sheath (147). The mechanical cable (146) can be translated relative to the sheath (147) on the arm base unit using a pneumatic cylinder, motor, or other means. Because the angle θ can be made arbitrarily small, there is an arbitrarily large mechanical advantage generated by using this mechanism, thus very high forces can be generated to expand the disks relative to each other. Another advantage of this mechanism is that the high-force contact points are rolling contacts, minimizing friction and thus minimizing the energy lost. Another advantage of this mechanism is that the actuator assembly and mechanical cable and sheath (146) (147) are easily sterilized for medical applications.

Figure 15:
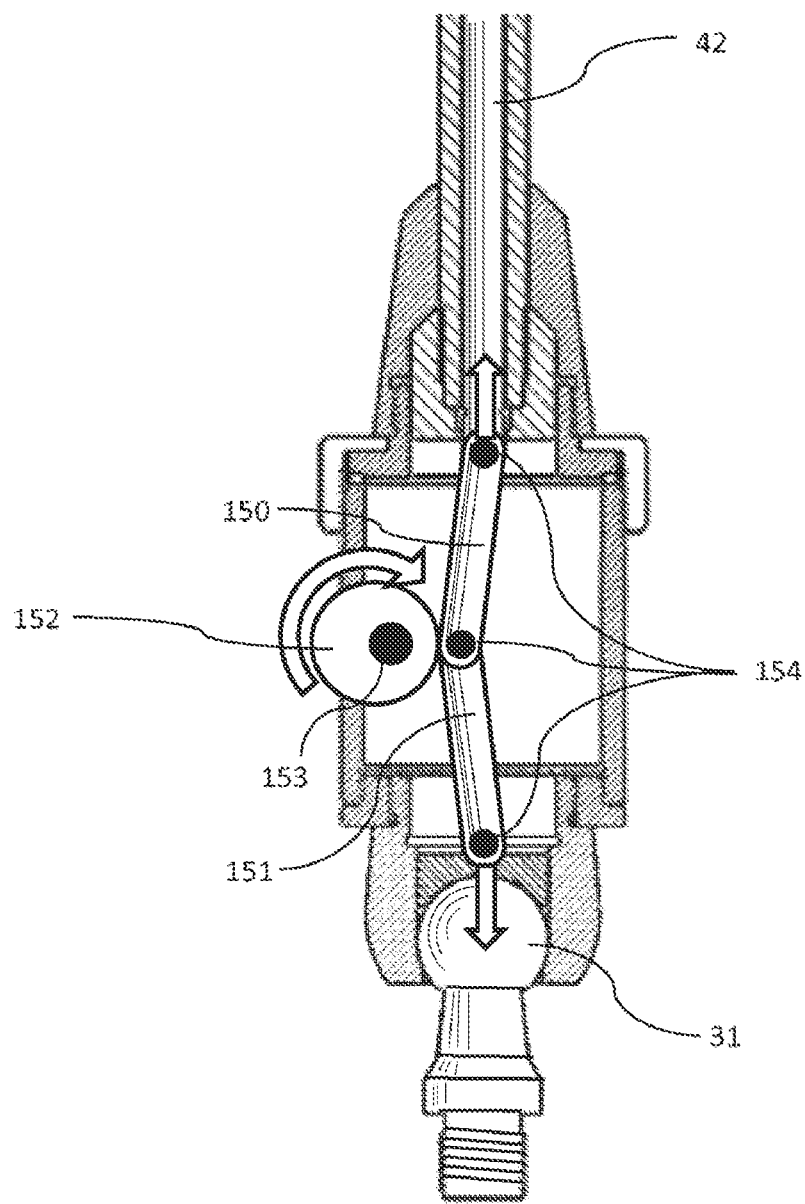
FIG. 15 shows a cross-sectional view of an alternate bilateral locking mechanism embodiment using linkage members and an eccentric hub to generate mechanical advantage.

In another embodiment of the bilateral actuator (shown in cross-section in FIG. 15), a mechanical linkage consisting of two links (150) (151) coupled together with three pins (154) is installed in-line with the upper base rod (42). In this embodiment, large mechanical advantage is achieved as the two links (150) (151) are pushed into alignment towards the medial direction. In this embodiment, the medial pushing is accomplished by an eccentric drive wheel (152) to create further mechanical advantage for locking the system. The axis of the eccentric drive wheel (153) may be rotated by a motor shaft, hydraulic means, or other means.

Figure 16:
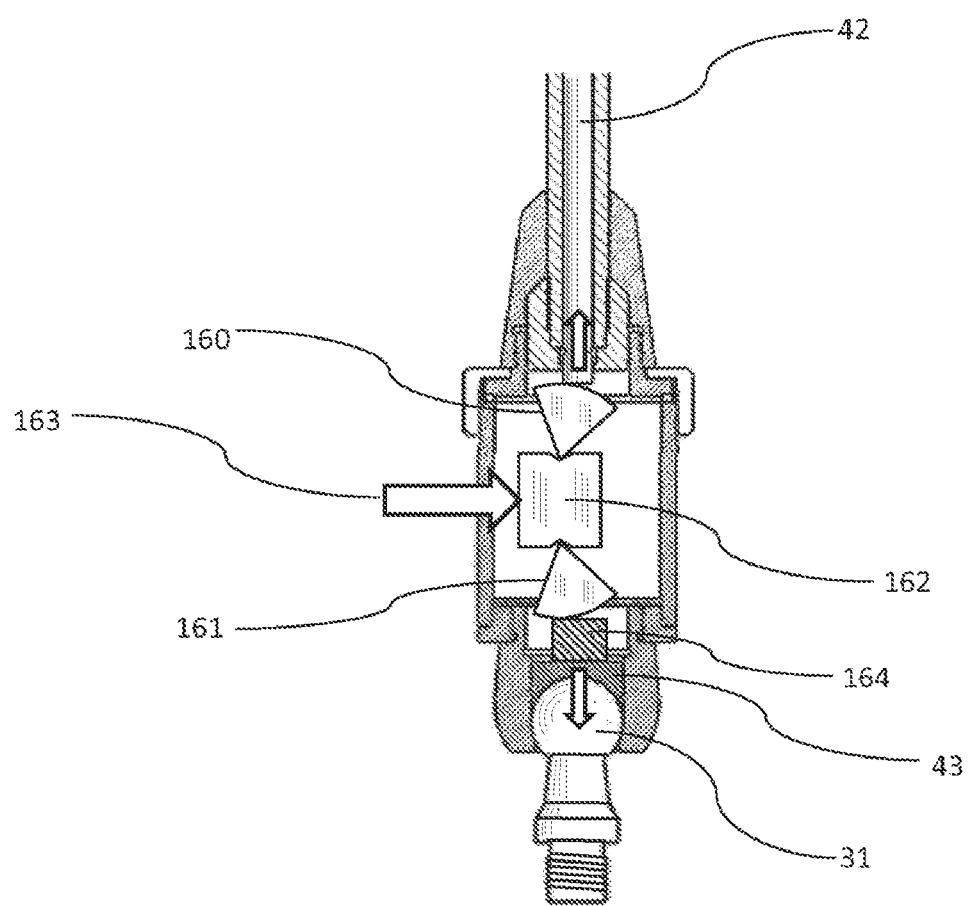
FIG. 16 shows a cross-sectional view of an alternate bilateral locking mechanism embodiment that uses roller wedges to create mechanical advantage.

In another embodiment of the bilateral actuator, a set of roller wedges (160) (161) may be used as shown in FIG. 16. A block with two notches (162) houses the tips of two roller wedges and is pushed medially with a force as shown by the arrow (163). The rolling surfaces of the wedges can be customized in order to generate a desired mechanical advantage of block motion to motion of the upper base rod (42) and a spacer block (164) rigidly fixed to the base friction block (43). The medial force (163) can be applied by any reasonable means including an eccentric hub, hydraulic piston, pneumatic piston, or other means.

Figures 17A, 17B, 17C, 17D:
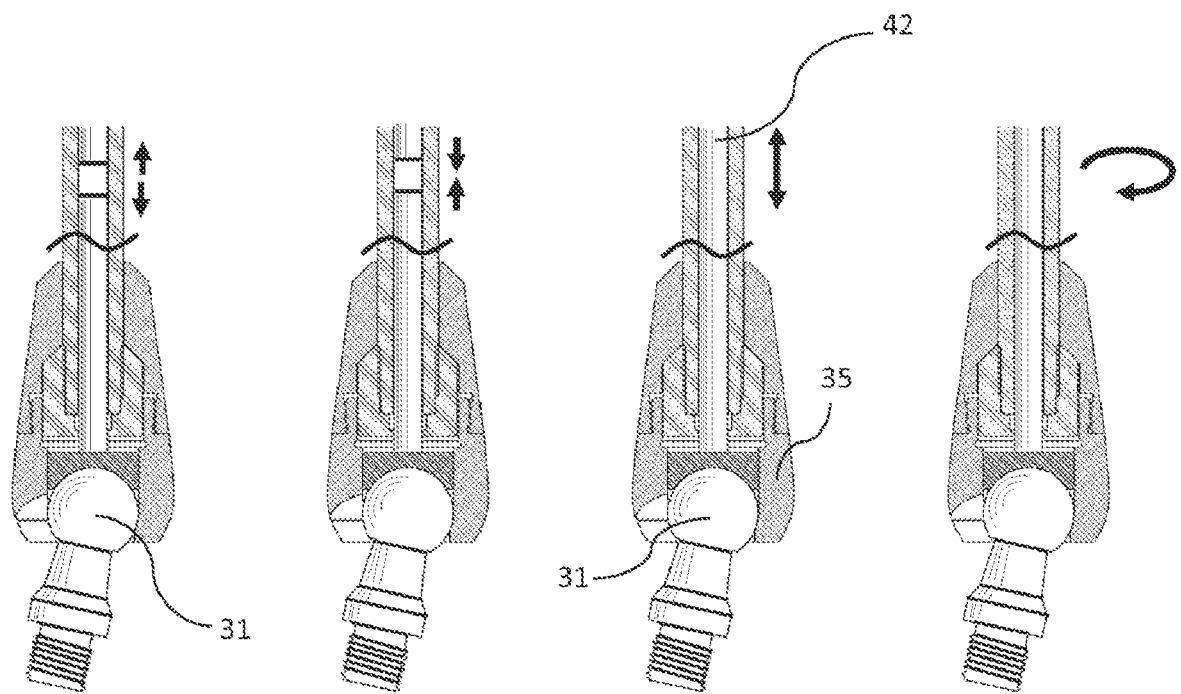
FIG. 17(a)-(d conceptually shows different ways for the locking mechanism to distribute locking force to the arm joints.

FIG. 17(a)-(d) conceptually depict various locking actuation means. FIG. 17a represents a bilateral force generator that exerts locking compression on the upper base rod(s) FIG. 17b represents a bilateral force generator that exerts locking tension on the inner rod(s). FIG. 17c represents a unilateral force generator that forces the inner rod in a single direction. FIG. 17d represents a locking mechanism that rotates the inner rod. These show schematically that the actuation through the upper base rod (42) may be made through any one of a variety of means. These include, but are not limited to, (a) expanding the inner rod length with a bilateral expanding actuator to cause compression of the upper base rod (42) as described previously in this application; (b) forcibly shortening the inner rod with a bilateral compressing actuator that places the upper base rod (42) in tension; (c) forcibly shifting the inner rod proximally or distally, thus putting different segments of the upper base rod (42) in compression and tension; (d) rotating the inner rod. For each of the upper base rod actuation concepts shown in FIG. 17, the joint locking means must be selected accordingly.

Figure 18A:
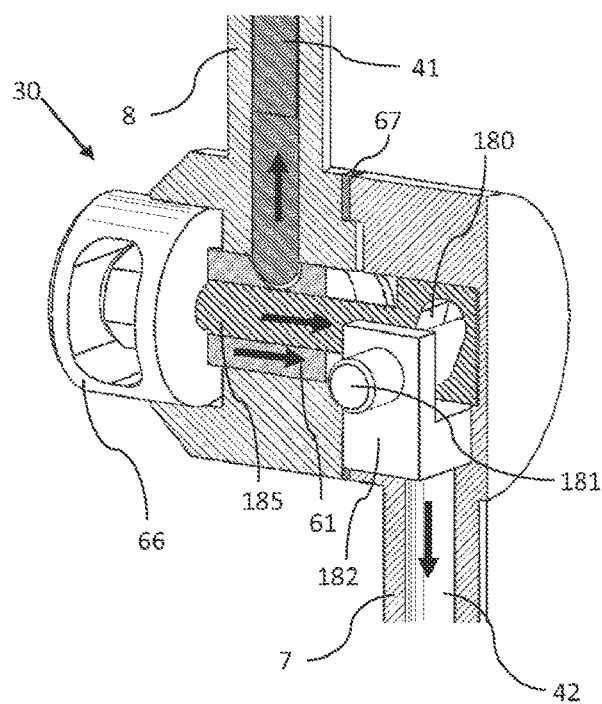
FIG. 18a shows a cross-sectional view of a center rotational joint that is locked by pulling the upper base rod in a direction away from the center rotational joint.

For the concepts depicted in FIG. 17a, as well as FIG. 17c where the upper base rod (42) actuates distally to lock the arm, the center rotational joint (30) is locked by applying compression forces on the upper base rod (42) as shown in FIG. 6. For the concepts depicted in FIG. 17b, as well as FIG. 17c where the upper base rod (42) actuates proximally to lock the arm, the center rotational joint (30) is locked by applying tension forces on the upper base rod (42). FIG. 18a shows a cross-sectional view of a center rotational joint (30) that actuates via tension force applied to the upper base rod (42). A ramped interface (180) cut into the axle member (185) accommodates a pin (181) attached to the upper base rod (42) via a bridge member (182). When the upper base rod (42) translates proximally, the pin (181) pulls the axle (185) towards the base arm segment (7). A nut (66) on the end of the axle (185) pushes the distal slug (61) towards the base arm segment (7), which causes both the distal inner rod (41) to actuate the distal joints, and the center rotational joint (30) to lock via compression force at the friction washer (67). Note that in FIG. 18a, the nut (66) is located on the distal side of the arm (as opposed to previous embodiments where it is on the base side) to accommodate the modified features on the base side of the center rotational joint (30).

Figure 18B:
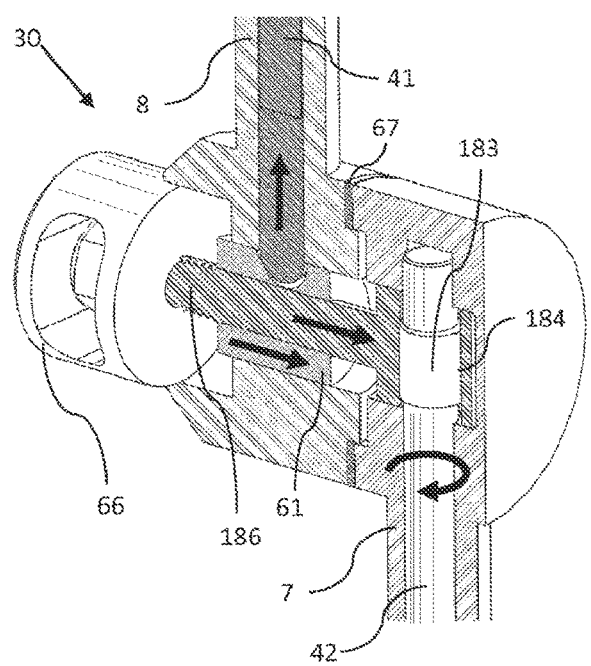
FIG. 18b shows a cross-sectional view of a center rotational joint that is locked by rotating the upper base rod.

For the concept depicted in FIG. 17d, the center rotational joint (30) and base spherical joint (31) are locked by applying rotational torque on the upper base rod (42). FIG. 18b shows a cross-sectional view of a center rotational joint (30) that actuates via torque applied to the upper base rod (42). An eccentric hub (183) rigidly fixed to the upper base rod (42) engages a slot (184) cut in the axle member (186). When the upper base rod (42) rotates, the eccentric hub (183) pushes the axle member (186) towards the base are segment (7). A nut (66) on the end of the axle (186) pushes the distal slug (61) towards the base arm segment (7), which causes both the distal rod (41) to actuate the distal joints, and the center rotational joint (30) to lock via compression force at the friction washer (67). Note that in FIG. 18b, the nut (66) is located on the distal side of the arm to accommodate the modified features on the base side of the center rotational joint (30).

Figure 19:
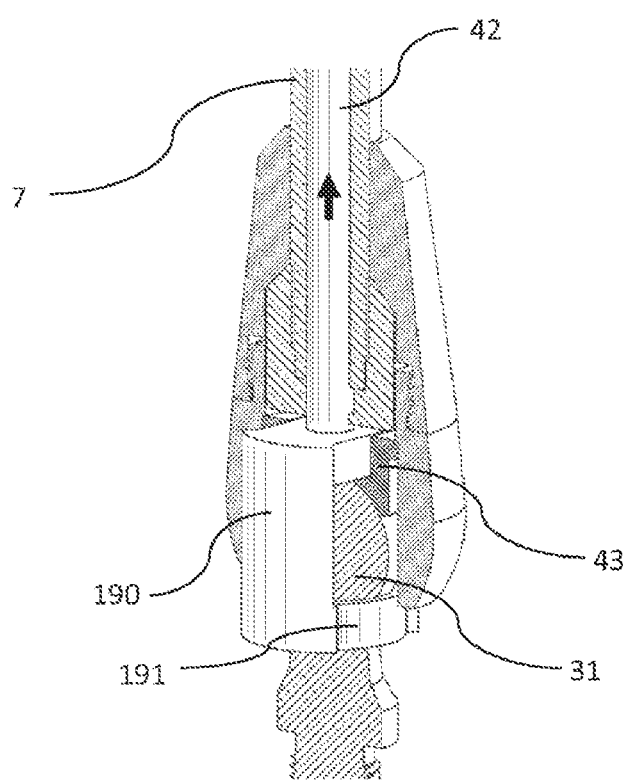
FIG. 19 shows a cross-sectional view of a spherical joint that is locked by pulling an inner rod in a direction away from the spherical joint.

For the concepts depicted in FIG. 17a, as well as FIG. 17c where the upper base rod (42) actuates proximally to lock the arm, the base spherical joint (31) is locked by applying compression forces on the upper base rod (42) as shown in FIG. 5. For the concepts depicted in FIG. 17b, as well as FIG. 17c where the upper base rod (42) actuates distally to lock the arm, the base sphere joint (31) is locked by applying tension forces on the upper base rod (42). FIG. 19 shows a cross-sectional view of a spherical joint (31) that actuates via tension force applied to the inner rod (42). A bridge member (190) connects the upper base rod (42) with a proximal friction cup (191) that contacts the proximal side of the base sphere (31). When the upper base rod (42) is pulled distally, the base sphere (31) is locked by means of compression between the proximal friction cup (191) and the base friction block (43).

Figure 20:
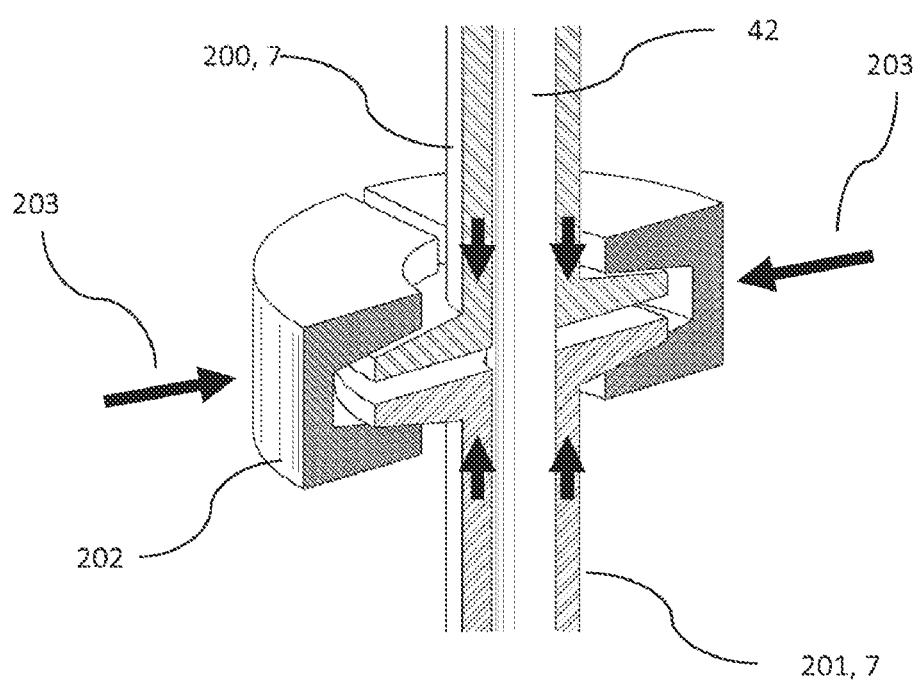
FIG. 20 shows a cross-sectional view of an alternate locking mechanism that exerts locking tension forces on an outer arm segment.

While previous examples concentrate on solutions where the internal rods perform the locking forces, it is also possible to lock the arm joints by manipulating the base arm segment (7) as shown schematically in FIG. 20. In this embodiment, the base upper base rod (42) is continuous and not acted upon by a locking member. Instead, a force or set of forces (203) are provided to pull two halves (200) (201) of the base arm segment (7) forcibly together. In this example, the actuation means is a ring of tapered clamps (202) that are forced inward. This style of actuation has the same effect on the base joints (30) (34) and center joint (30) as the bilateral force generator concept depicted in FIG. 17a, which effectively places the inner rod in compression and the base arm segment (7) in tension. Note that a related embodiment is possible (not shown) where the base arm segment (7) is forcibly placed in tension by an actuator, which has the same effect as the bilateral force generator concept depicted in FIG. 17b.

Figure 21A:
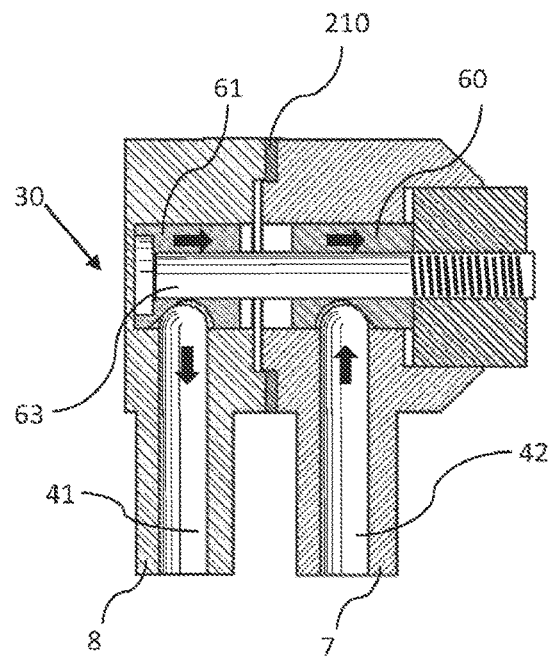
FIGS. 21a-d show cross-sectional views of alternate embodiments of the center rotational joint of FIGS. 1-4.
Figure 21B:
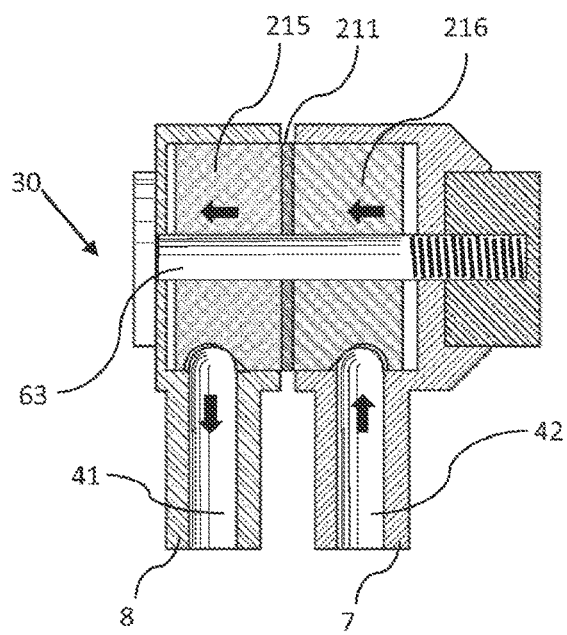
Figure 21C:
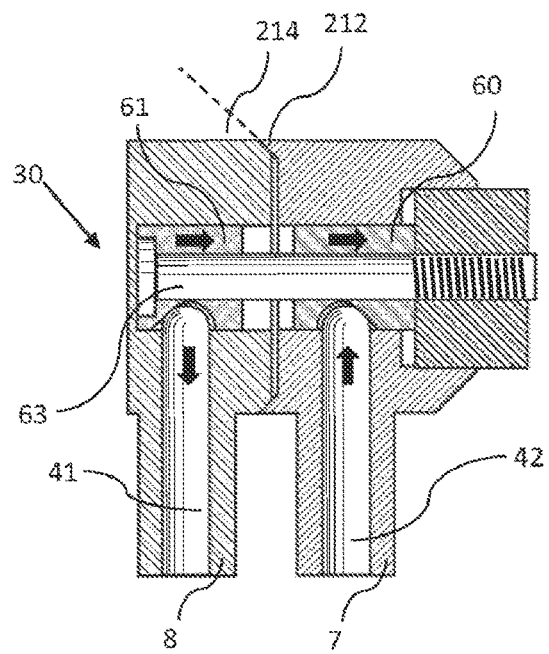
Figure 21D:
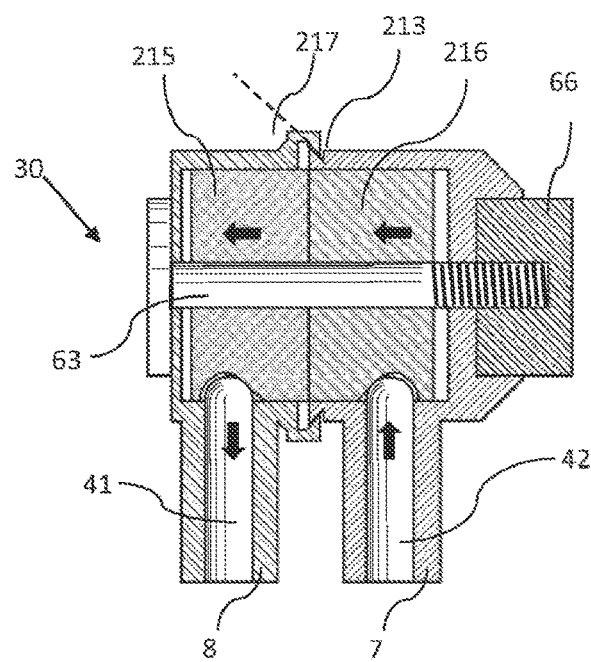

In the foregoing embodiments, the components inside the central joint (30) may be configured in multiple ways. Several variations are shown in FIG. 21. FIG. 21a shows the primary embodiment of FIGS. 1-4 where the base slug is pushed laterally away from the center of the joint. FIG. 21b shows an alternative embodiment where the base slug is pushed medially towards the center of the joint. FIG. 21c shows an alternative embodiment of FIG. 21a where a conical joint interface is used for generating increased friction. FIG. 21d shows an alternative embodiment of FIG. 21b where a conical joint interface is used for generating increased friction. In the embodiments of FIGS. 18(a) and (c) the actuated inner base rod (42) forces the slugs (60) (61) towards the base arm segment (7), whereas in the scenarios (b) and (d) the inner base rod (42) forces the slugs (215) (216) towards the distal arm segment (8). In each case the slug ramp interfaces are selected to achieve a particular direction of slug motion. In FIG. 21a, b, the rotational joint interface (210) (211) is flat, where in (c) and (d) the interface is conical (212) (213) at angle $\theta$ (214) (217). For conical angles $\theta$ (214) (217) in the approximate range 3 degrees to 85 degrees, a rotational locking advantage is achieved, and less force is required to prevent relative rotation of the base (7) and distal (8) sides of the arm. The other advantage of the conical angle is that it automatically aligns the joint together concentrically, minimizing any play or backlash in the joint. In FIG. 21b, the joint interface is flat and axle (63) end caps prevent the base arm and distal arm from separating. Here, the slugs have large diameter (215) (216) because the primary locking force of the joint comes from the frictional interface (211) between the slugs. In FIG. 21d, a conical interface retains the two sides of the joint at angle $\theta$ (217) generates advantageous friction forces.

Figure 22A:
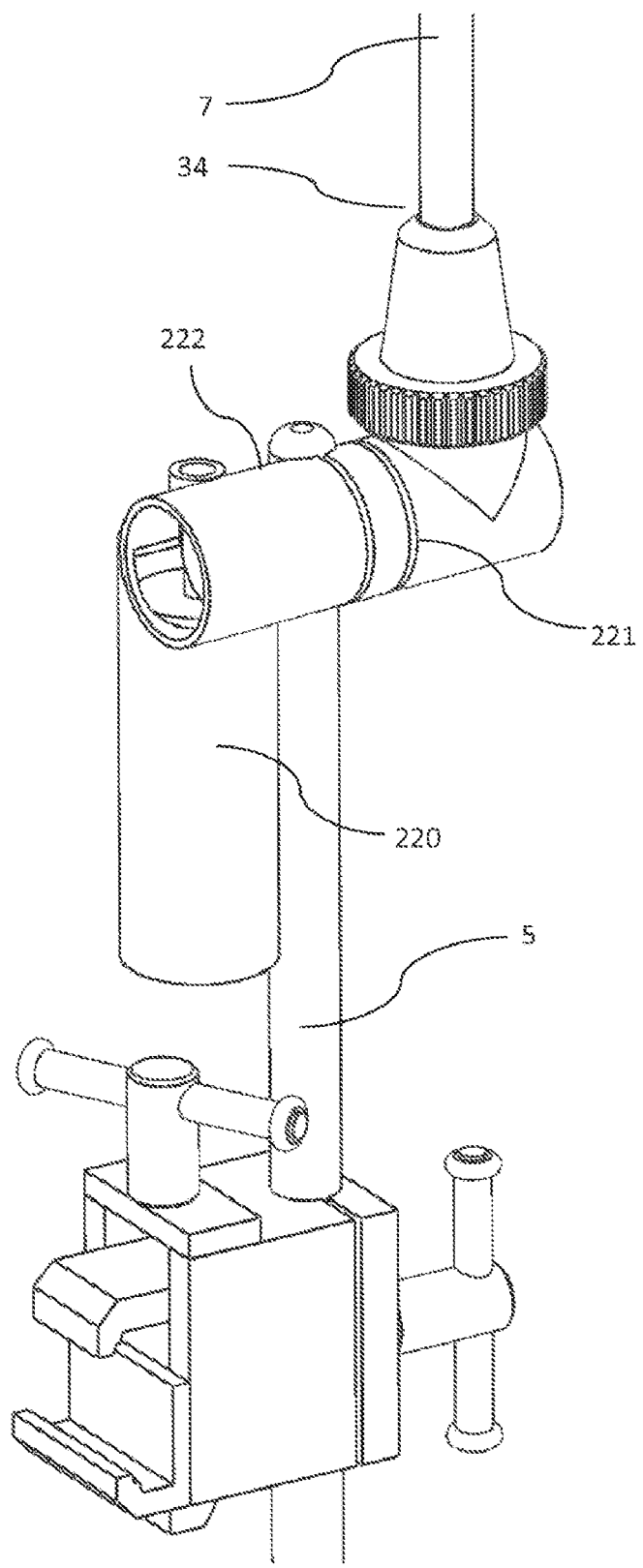
FIGS. 22a and 22b shows alternative embodiments of the proximal portion of a repositionable, lockable support arm where the locking mechanism latches and is located at the base of the arm.

In the foregoing embodiments, the actuator (6) was shown positioned between the base spherical joint (31) and the center rotational joint (30). In some alternative embodiments, an actuator can be located distal to the base joint (31). In one embodiment shown in FIG. 22a, the actuator is combined with a base unit (220). A first rotatable base joint (221) and a second orthogonal rotatable base joint (222) enable two degrees of rotational freedom proximal to the base rotational joint (34). The clamp to the pole (5) can be a split clamp or internal moving slug.

Figure 22B:
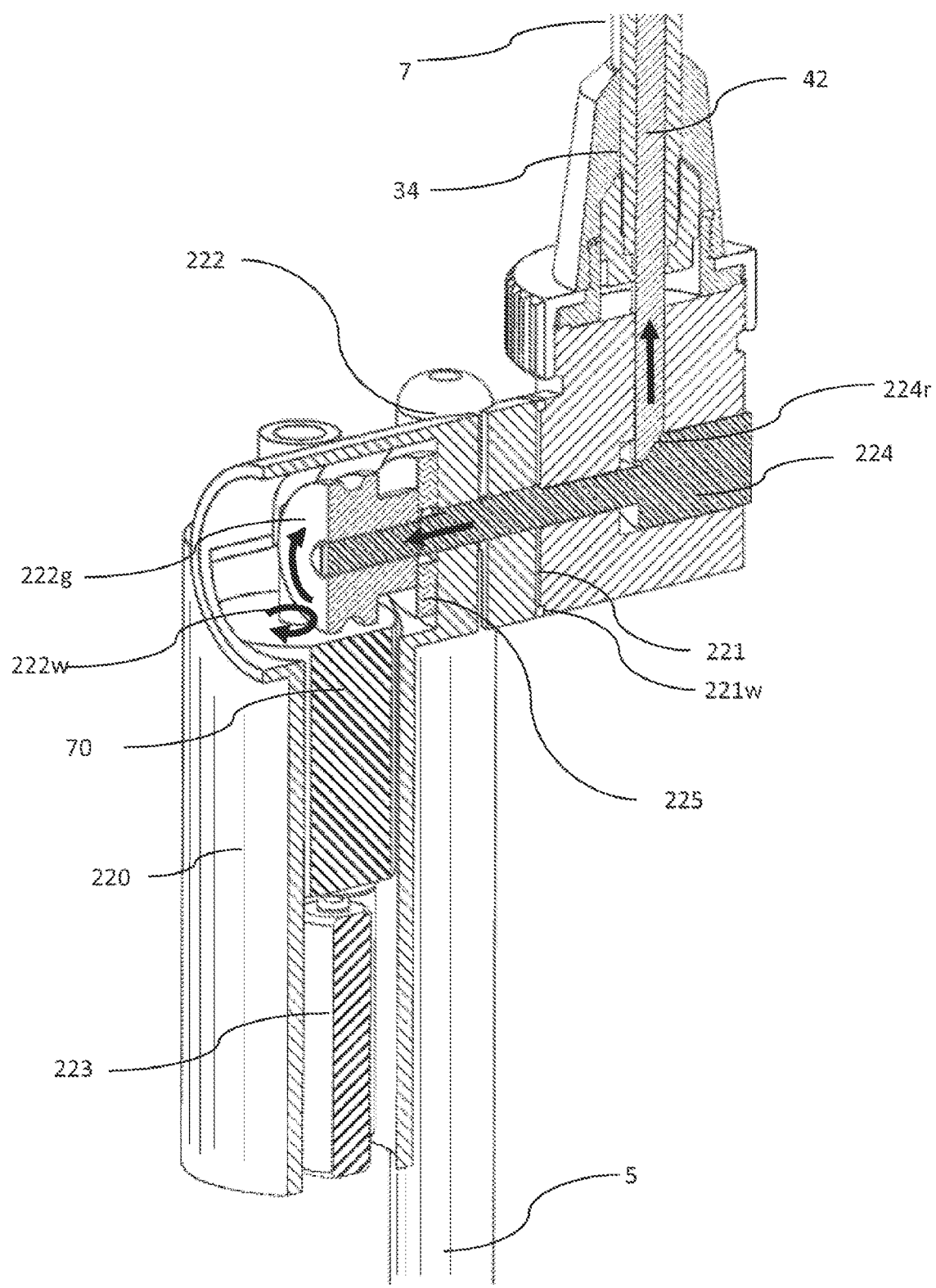

FIG. 22b shows a cross-sectional view of the combined base actuator (220) and its internal components. This embodiment includes a battery pack 223 and an electric motor (70). A force multiplier is implemented, consisting of a worm (222w) coupled to the motor shaft and a mating worm gear (222g). When tightened, the worm gear (222g) is held in place axially by a thrust bearing (225) as it pulls a threaded axle member (224) towards the motor (70). This pull locks the rotatable clamp joint (222) and the rotatable base joint (221). The rotatable base joint (221) locking force is enhanced by friction washer (221w). The pull on axle (224) also pulls a ramp surface (224r) engaging the bottom of upper base rod (42) thus transferring locking force to the joints distal in the arm.

Figure 23:
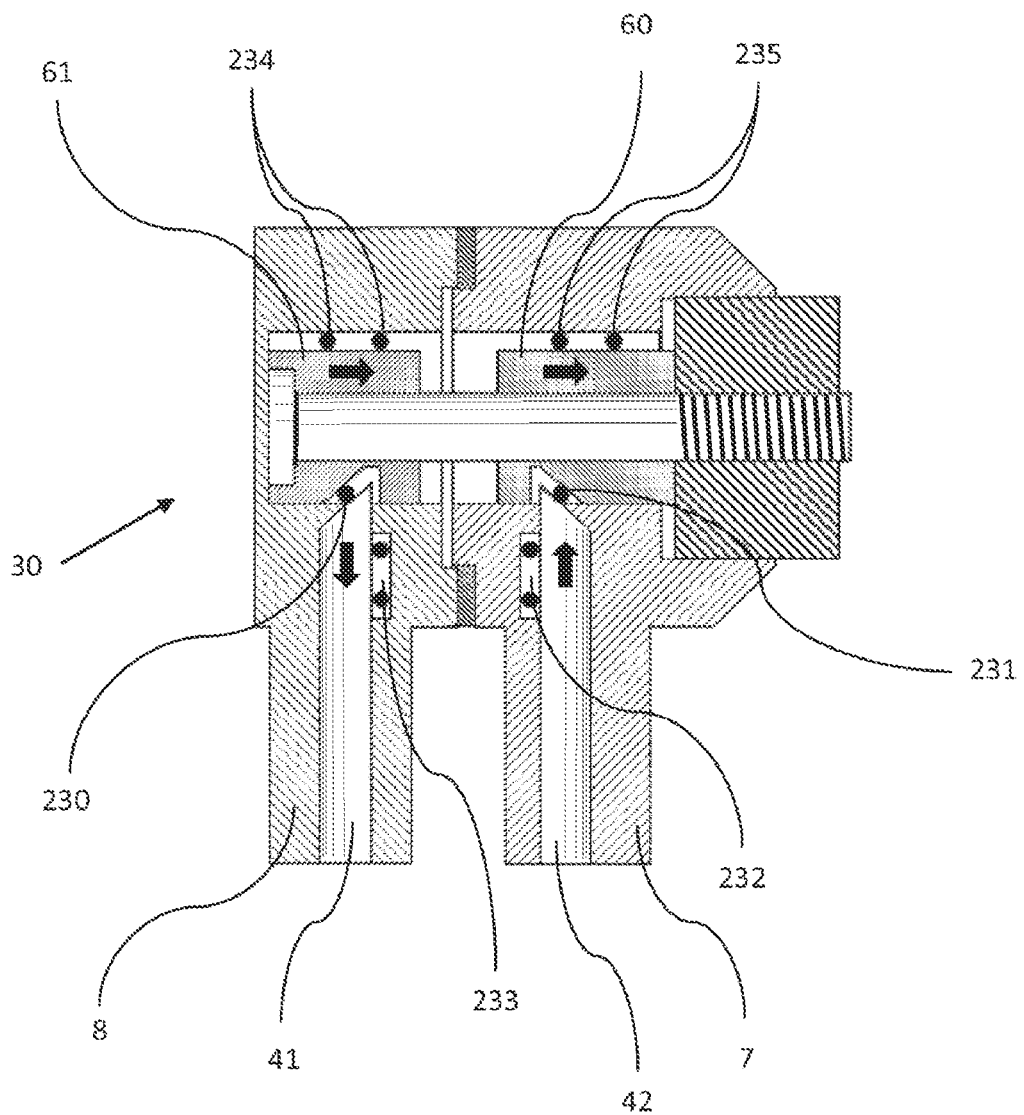
FIG. 23 is a cross-sectional view of an alternative embodiment of the center rotational joint of FIGS. 1-4 where rolling elements are used to reduce frictional energy losses.

In the previous embodiments and in commonly practiced prior art, the mechanical elements of the arm can experience substantial loads. Several of the elements must slide under the applied load. The mechanical work done dragging these elements is not recovered each cycle. Therefore this energy must be supplied by a source such as a battery or CO2 cartridge. The magnitude of the lost energy in part determines the size of the battery, cartridge, and other energy-related elements. In an effort to minimize the lost energy, some or all of the sliding contacts may be replaced by rolling contacts FIG. 23 schematically depicts this concept to the details of the center joint (30). Cylindrical rollers (230) and (231) are provided to replace the sliding contacts of the rod interfaces (41r) and (42r). The sliding load on the slugs (60) and (61) is also mitigated by providing rollers (234) and (235). The sliding contact of the inner rods (42) and (41) on arm segments (7) and (8) is replaced with rollers (232) (233) as well.

Figure 24:
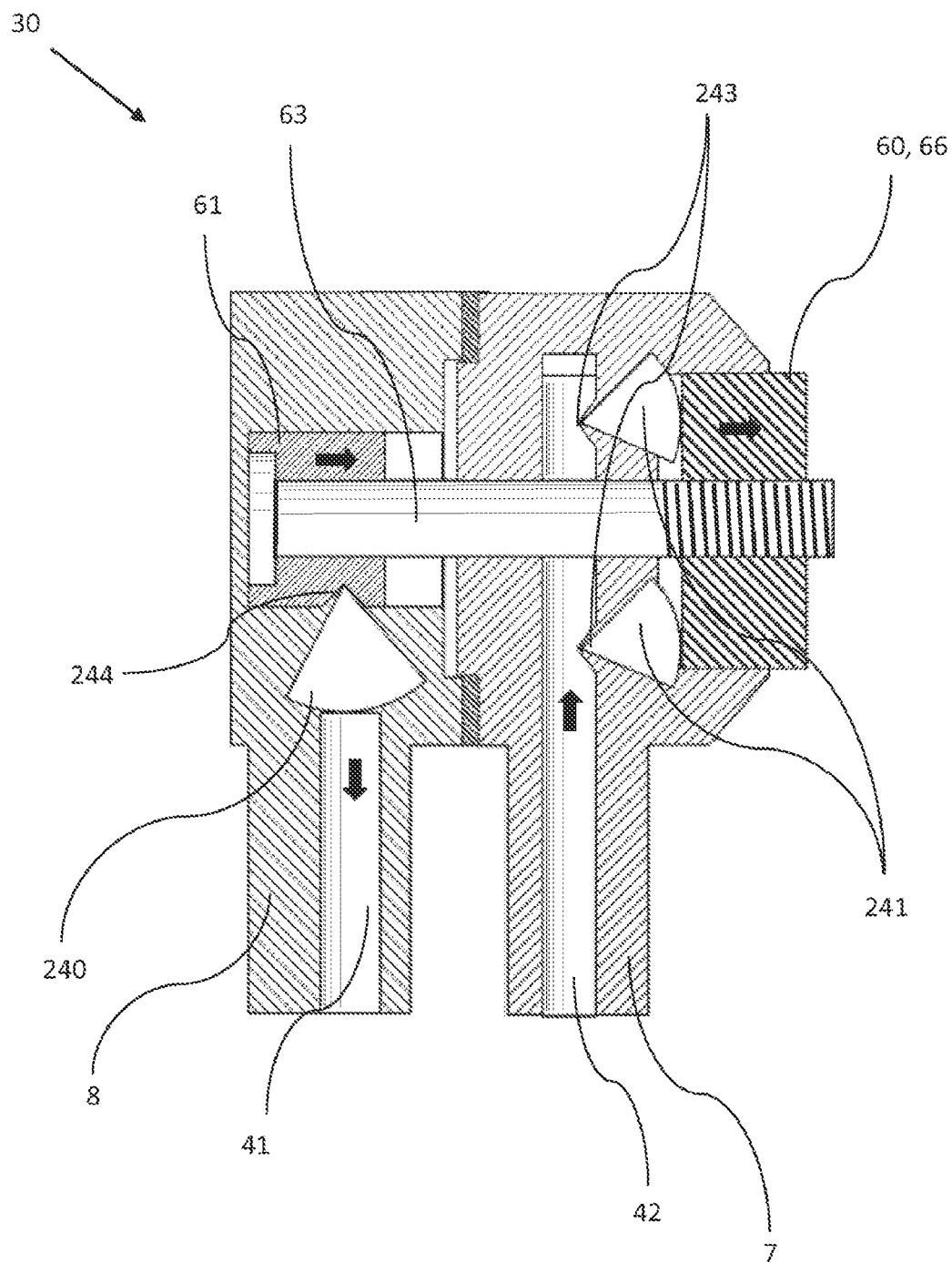
FIG. 24 is a cross-sectional view of an alternative embodiment of the center rotational joint of FIGS. 1-4 where roller wedges are used to reduce frictional energy losses and generate mechanical advantage.

In another variation (FIG. 24) of the center joint (30), roller wedges (240) and (241) are used to interface between the inner rods (41) (42) and slugs (60) (61). Such wedges may also be used in conjunction with rollers (not shown) as in FIG. 23. In this embodiment, a pair of notches (243) are cut into the upper base rod (42). As the upper base rod (42) is pushed up, a lateral translation occurs to the base slug (60) because of the placement of the base roller wedges (241) and notches (243). Through the capped axle member (63), a translation is imparted to the distal slug (61) which contains a separate notch (244). The motion of the distal slug notch (244) rotates the distal rolling wedge (240). The arc of the distal rolling wedge (240) pushes on the end of the distal inner rod (41) and actuates the distal arm joints. This system has the advantage of producing a rolling contact between the roller wedge and compression rod, decreasing frictional losses. In addition this approach allows a customizable mechanical advantage according to the shape of the rolling surface. The shape of the rolling surface determines the ratio of motion between the slugs and the inner rods, so customizable mechanical advantage can be achieved. Note that in FIG. 24, the threaded knob (66) effectively acts as the proximal slug (60).

It is important that "slop" in each joint of the arm is minimized such that when the arm goes from an unlocked to locked state, the instrument's position does not change. To minimize this "jump" it is common in the art to minimize the clearance at each joint. Each joint may be pre-loaded with a suitable spring to eliminate the clearance.

Figure 25A:
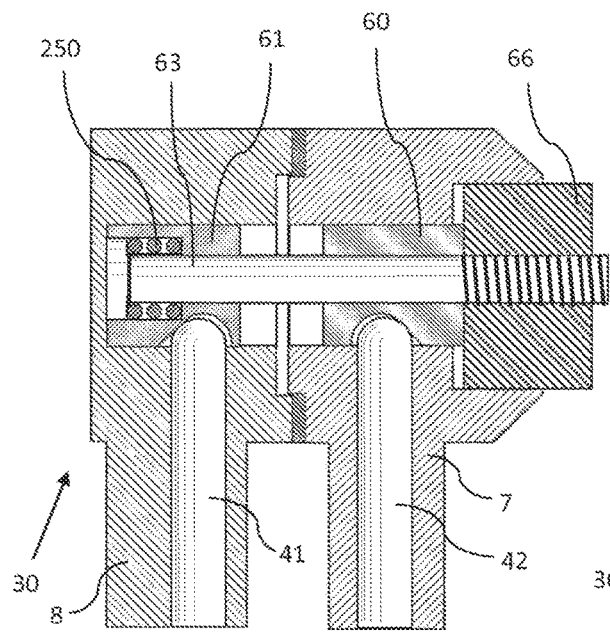
FIG. 25a-h show cross-sectional views of various embodiments for preloading the joints of a repositionable, lockable support arm.
Figure 25B:
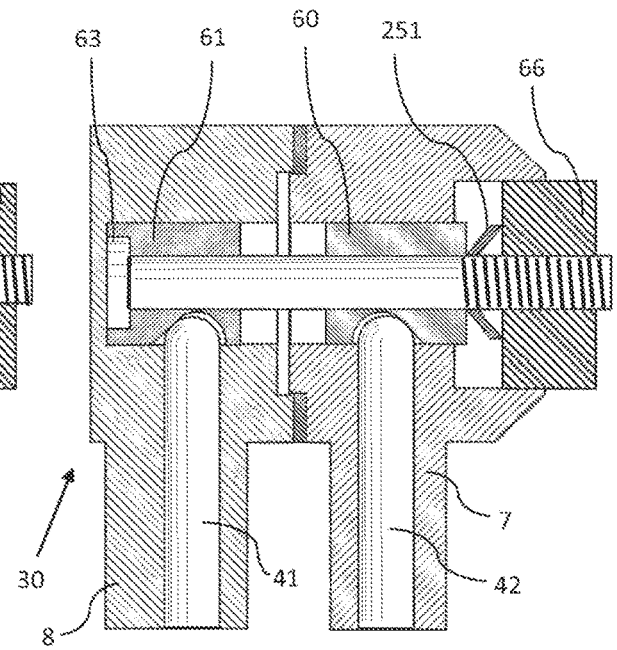

To minimize slop in the center rotational joint (30), a spring can be added in one or more carefully chosen places FIG. 25a shows a spring (250) between the capped axle member (63) and distal slug (61). When the arm is locked (e.g. compressive load is applied to the upper base rod (42) using an actuator (400)), the spring (250) is fully compressed and acts like a rigid element. When the actuator (400) is not in locking position, the spring (250) loads the upper base rod (42), distal rod (41), and center joint (30), eliminating all joint clearances in the arm. This also puts a small frictional load on each joint which may be selected to enhance the feel of the arm motion. FIG. 25b shows a similar arrangement but a spring (251) is located between the proximal slug (60) and the threaded knob (66). Again, in this arrangement the spring (251) loads the upper base rod (42), distal rod (41), and center joint (30), eliminating all joint clearances in the arm when the actuator is not in locking configuration.

Figure 25C:
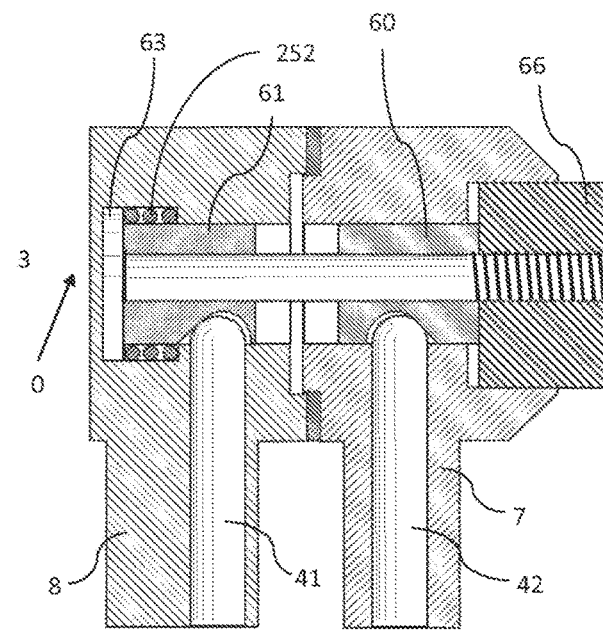
Figure 25D:
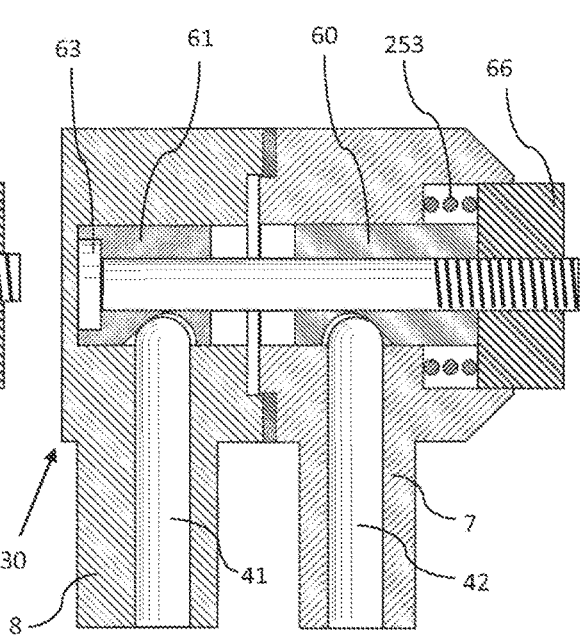

In some embodiments it is desirable to have preload in some joints and not preload in other joints. Two example the arrangements illustrated in FIG. 25c and FIG. 25d. In FIG. 25c a spring (252) loads the capped axle member (63) relative to the distal arm segment (8). This configuration loads the center rotation joint (30) and upper base rod (42), but does not load the distal rod (41) and thus does not load the distal rotational joint (33) and distal spherical joint (32). In FIG. 25d the situation is reversed. A spring (253) located between the threaded knob (66) and the base arm segment (7) loads the center rotational joint (30) and distal rod (41), but does not load the upper base rod (42) and thus does not load the base rotational joint (34) and base spherical joint (31).

In other embodiments, the center joint spring can act independently, without putting any pressure on the base or distal rods (41) (42) or slugs (60) (61). One way to achieve this (FIG. 25e) is to have an outer capped axle (255) that slides relative to an inner dual capped axle member (256), and a spring (254) that pushes on the dual capped axle member (256) relative to the distal arm segment (8). This places a compressive load between the base and distal arm segments (7) (8) which preloads the center rotational joint (30) without interfering with the slugs (60) (61). An alternate method to achieve this objective is to use magnets. By way of example, FIG. 25f shows a set of ring magnets (257) that exert attractive forces between the base and distal arm segments (7) (8), thus preloading the center rotational joint (30) without interfering with the slugs or rods.

Figure 25E:
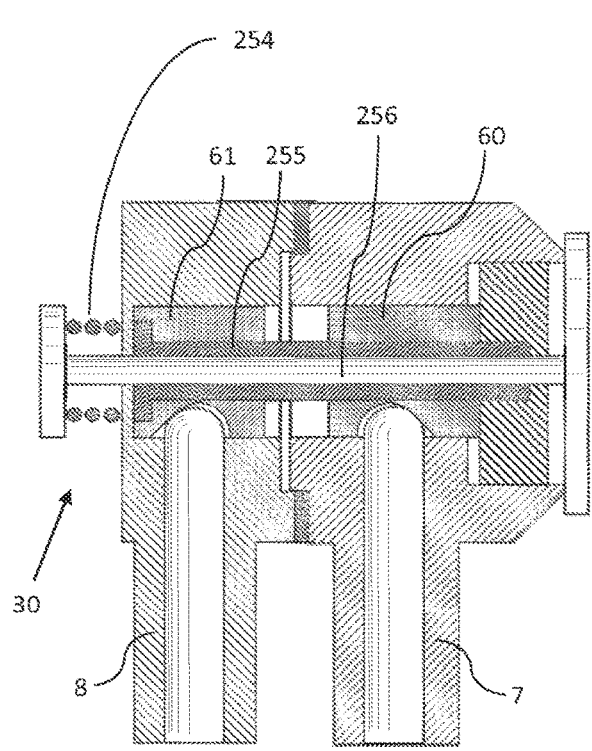
Figure 25F:
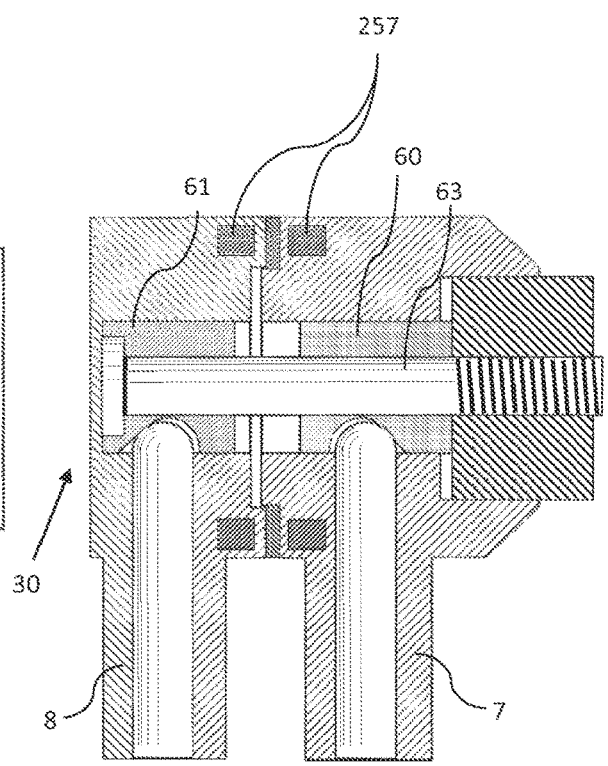
Figures 25G, 25H:
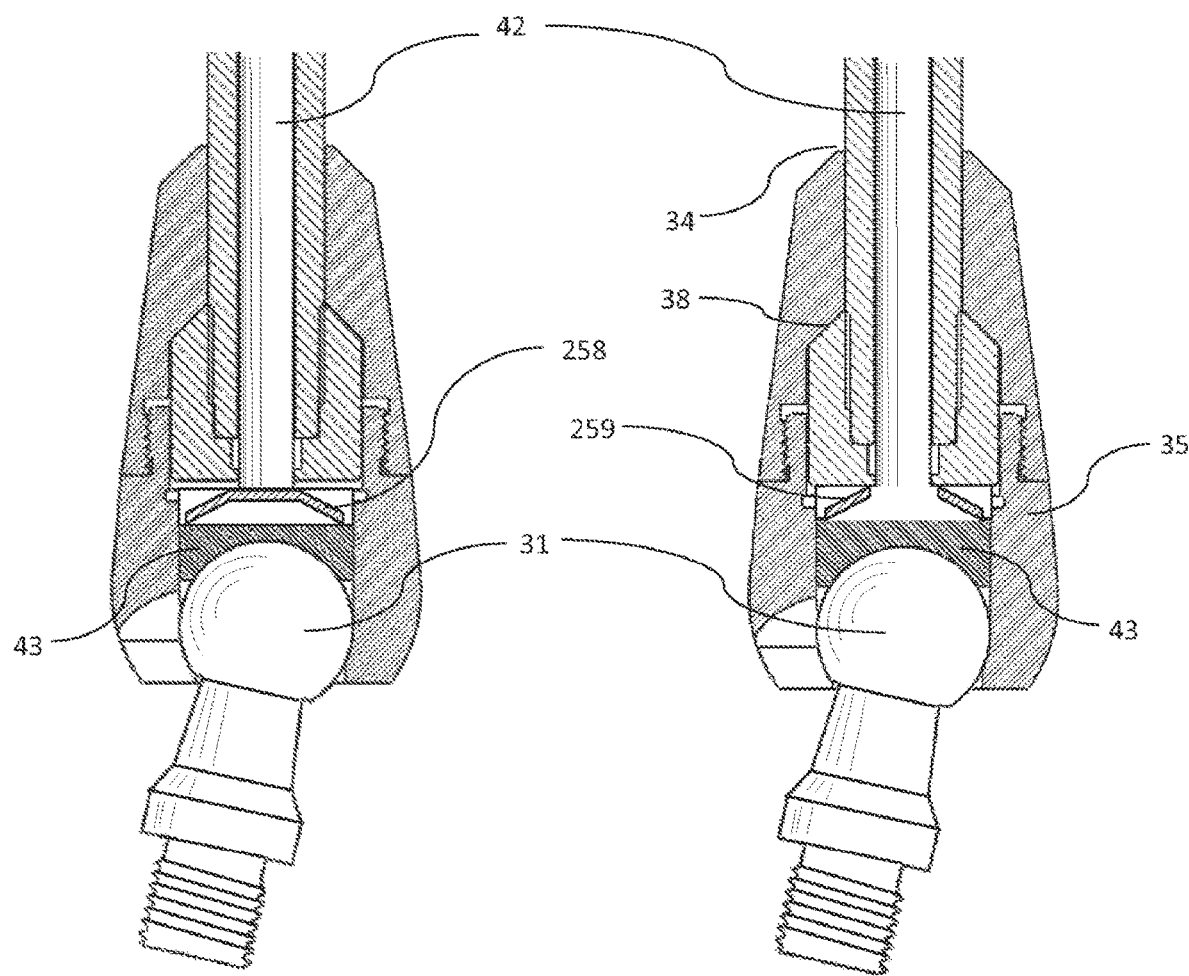

Alternately or in conjunction with the preloading designs described above, the base and distal spherical joints (30) (31) may be pre-loaded with a spring FIG. 25e depicts a disk spring (258) between the upper base rod (42) and the base friction block (43). The disk spring (258) preloads the upper base rod (42) when the actuator (400) is not in a locking configuration, thus effectively preloading all joints in the arm simultaneously. Disk springs have the property that they may be pushed "flat" when loaded with high force, and so may act as a rigid element when the actuator (400) is in locking configuration and the arm joints are locked. To preload only the base spherical joint (31) and base rotational joint (34), FIG. 25h shows another embodiment where an annular spring (259) provides a load between the base friction block (43) and the base spherical joint retainer (35). The upper base rod (42) passes through this spring (259) without transmitting load, so the central rotational joint (30) and distal joints receive no preload. An equivalent design can be applied to preload only the distal spherical joint (32) and distal rotational joint (33).

Figure 26A:
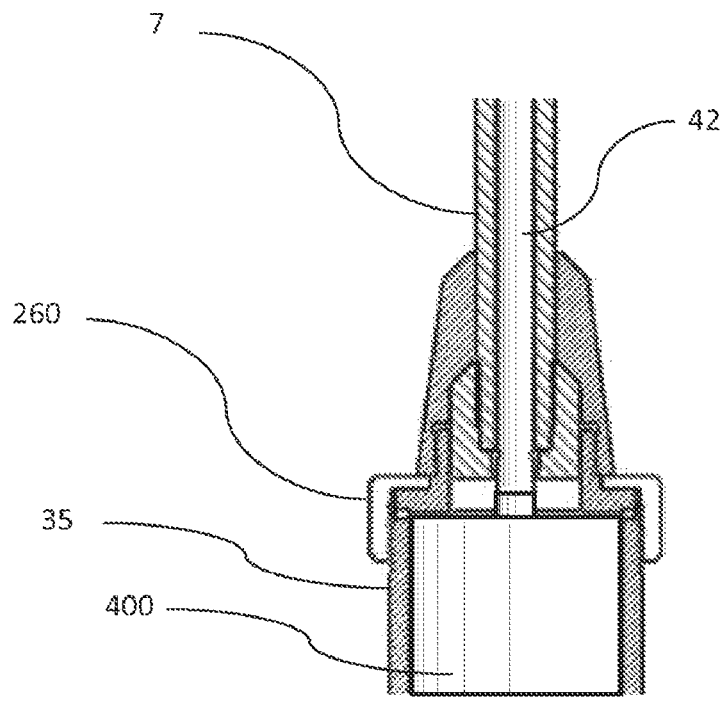
FIG. 26a-b show cross-sectional views of two alternative embodiments for mechanical override lock/release systems for a repositionable, lockable support arm.
Figure 26B:
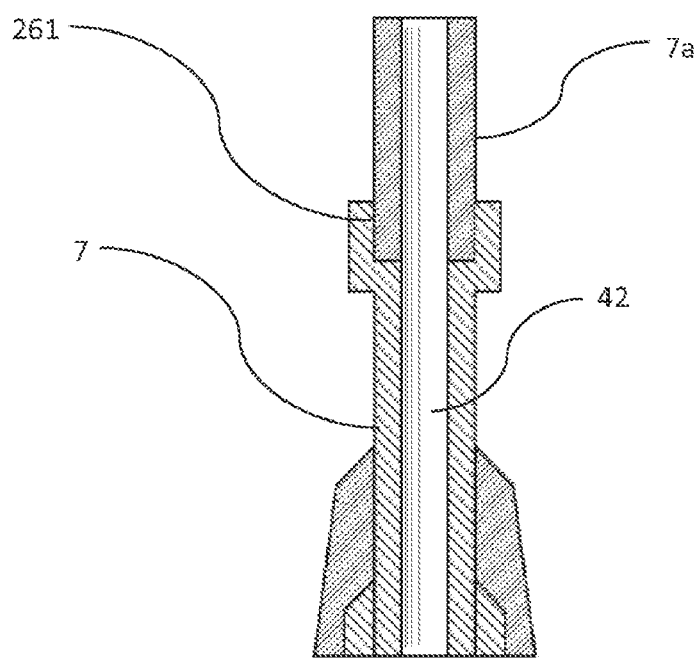

FIG. 6 introduced the detailed features of the central rotational joint (30). One of the functions was to provide a manual mechanical override knob (66) in case of actuator failure. FIG. 26a and FIG. 26b show alternate mechanical override methods. In FIG. 26a a threaded coupler (260) connects the base arm segment (7) to the distal spherical retainer body (35). This effectively provides a method to relieve or apply pressure between the actuator unit (400) and upper base rod (42), which can lock and release the joints of the arm independent of the actuator (400) state. FIG. 26b shows an alternate threaded coupling (261) located between the base arm segment (7) and a connecting base arm segment (7a). The purpose of the alternate threaded coupling is to effectively extend or retract the overall length of the base arm segment (7), thus manually locking and unlocking the arm joints independent of the actuator (400) state.

Figures 27A, 27B:
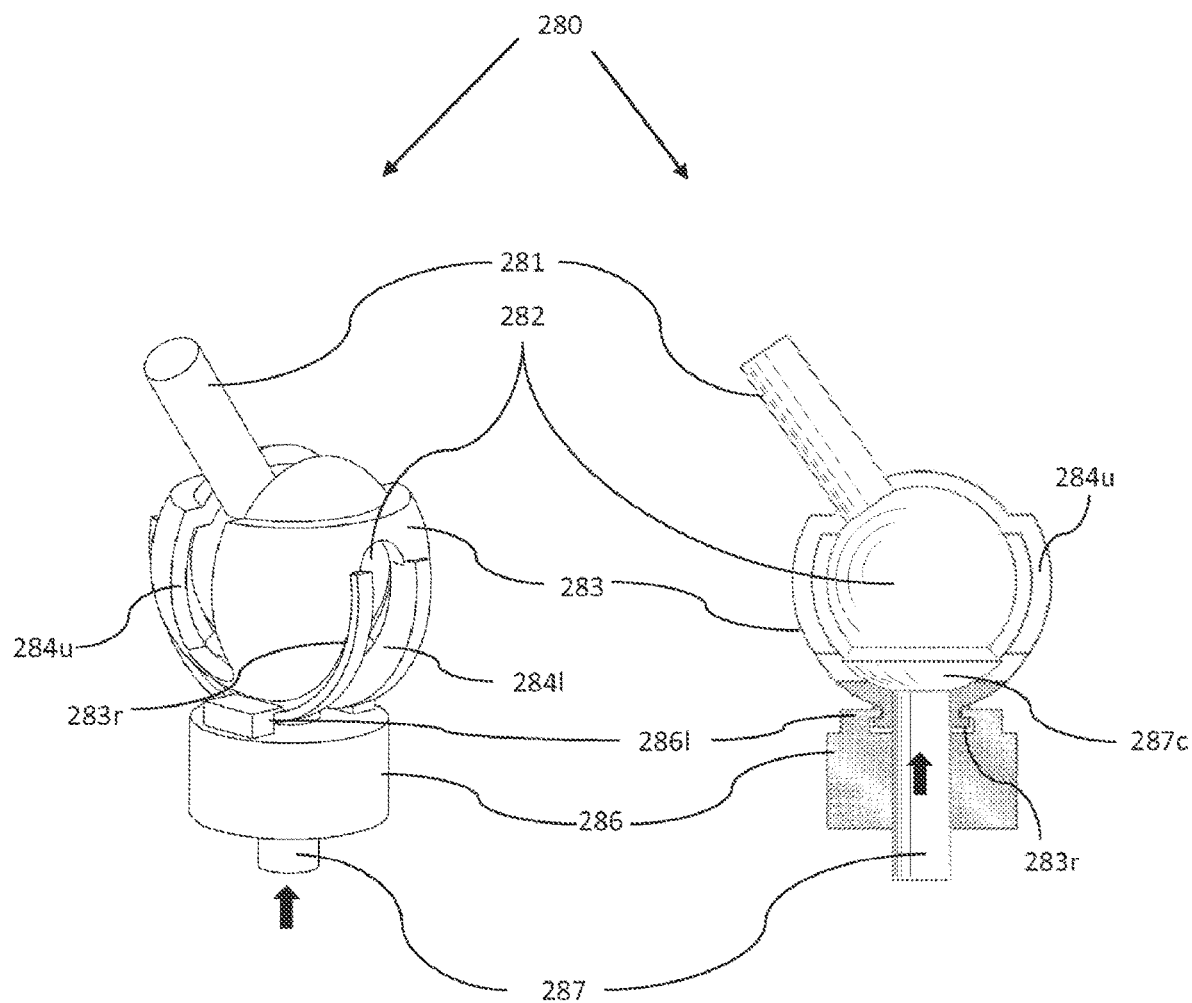
FIGS. 27a and 27b show an alternative embodiment for a locking spherical joint with increased range of motion that may be combined with a repositionable, lockable support arm in accordance with the present invention.

In another embodiment shown in FIG. 27, a double-slotted locking spherical joint (280) may be used instead of a typical locking spherical base joint (31) or distal joint (32). The advantage of this joint (280) is that the range of motion is increased relative to a typical spherical joint without having to manually rotate a spherical retainer (36) to match a spherical stem (37s) with a slot (37) (reference FIG. 5). Now with reference to FIG. 27, the double slotted locking spherical joint (280) can lock in place by actuating the push rod (287) of the cup part (287c) relative to the base (286), causing the spherical part (282) to be clamped between the outer casing (283) and cup part (287c), thus locking the sphere (282) and sphere stem (281) with respect to the base (286). A ridge feature (283r) on the outer casing (283) engages a lip feature (286l) on the base (286), connecting the outer casing (283) with the base (286) with a first rotational degree of freedom. The lower slot (284l) provides clearance for the push rod (287). An upper slot (284u) allows the sphere stem (281) to rotate substantially orthogonal to the first rotation. Each slot (284l) (284u) is cut sufficiently long such that the spherical stem (281) and push rod (287) have a large range of motion before contacting the edges of the slots.

Note that in all of the locking systems described herein, it is possible to "partially" actuate the system to produce an intermediate friction state between "fully locked" and "fully released". In hydraulic and pneumatic actuation systems, this can be achieved by applying variable pressure to the hydraulic or pneumatic cylinders. In the mechanical actuation systems, this is achieved by partially deploying the motor or mechanical system. The partially locked state can be used to enable fine positioning of the arm, as adding resistance to the arm joints makes fine motions of the arm easier to control by hand. In one workflow, when the instrument being held by the arm is close to its final position, the arm can change from fully unlocked to partially locked. After precision adjustments of the instrument using the partially resistive state of the arm, the arm can be fully locked into final position with full force.

As previously mentioned, arm lock/unlock button or switch (12, FIG. 1) is preferably placed near the distal end of the arm to enable one-handed instrument manipulation and unlocking/locking. The button or switch alternatively be placed on the floor (foot pedal), near the proximal base of the arm, or other locations. Another interesting place to put the button is on or near the center rotational joint (30). This way, the user is sure to be touching the center rotational joint (30) of the arm when unlocking the arm to prevent it from collapsing due to gravity whenever the arm is unlocked.

Figure 28A:
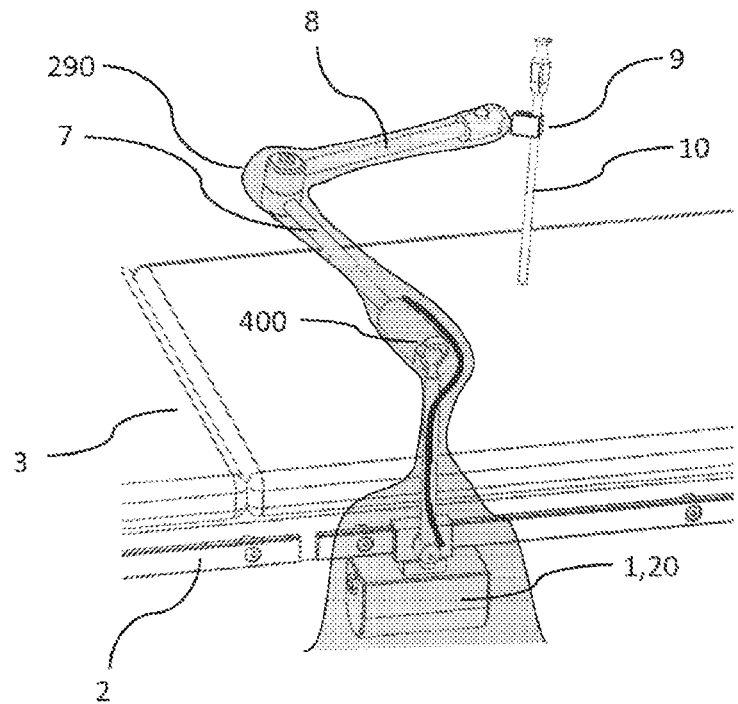
FIGS. 28a and 28b show two embodiments for sterilization systems for a repositionable, lockable support arm in accordance with the present invention.
Figure 28B:
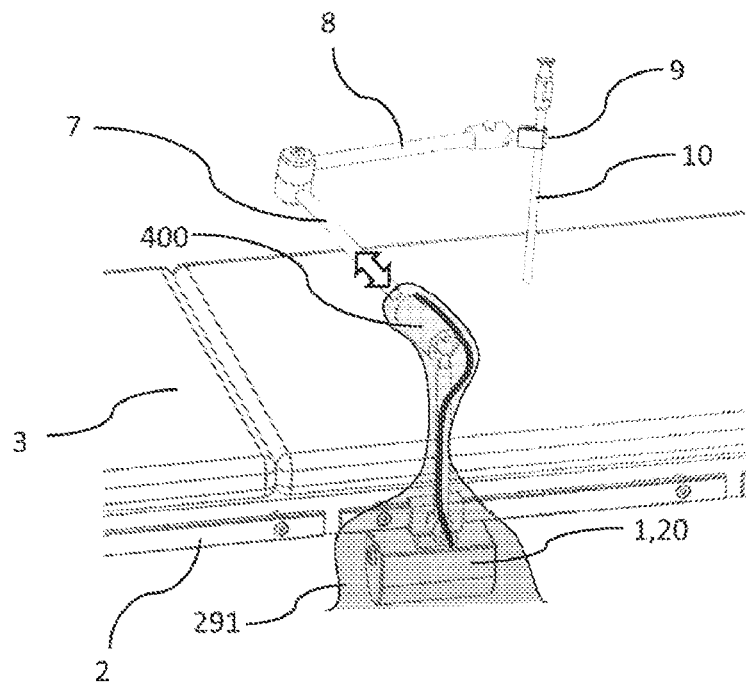

In many medical environments, sterilization of equipment is often desirable. In some arm embodiments it is feasible to sterilize the entire arm system, such as the direct CO2-powered embodiment shown in FIG. 11 or embodiments actuated with cable-actuated roll ball disks (FIG. 14). In other embodiments, it is desirable to not expose certain elements of the arm (hydraulic fluid, seals, etc.) to the harsh sterilization process. FIG. 28a and FIG. 28b show two alternative methods to keep the arm sterile in the operating environment. In FIG. 28a the entire arm including actuator (400), base arm segment (7), distal arm segment (8), and base unit ((1) or (20)) is draped with a thin sterile sleeve (290). The drape can terminates at the sterile instrument holder (9) at a drape interface (not shown), and the instrument (10) can be sterile. In FIG. 28b, only the base unit ((1) or (2)) and actuator locking mechanism (400) are covered with a drape (291). The portion of the arm distal to the actuator (400) including the base arm segment (7), distal arm segment (8), and instrument holder (9) can be sterilized using steam, chemicals, or other methods. The embodiment of FIG. 28b is desirable because the part of the arm that is closest to the operating site is not draped, thus remains very compact and slender where space is critical. This embodiment (FIG. 28b) relies on the fact that the distal portions of the arm can be detached from the actuator (400).

Figures 29A, 29B:
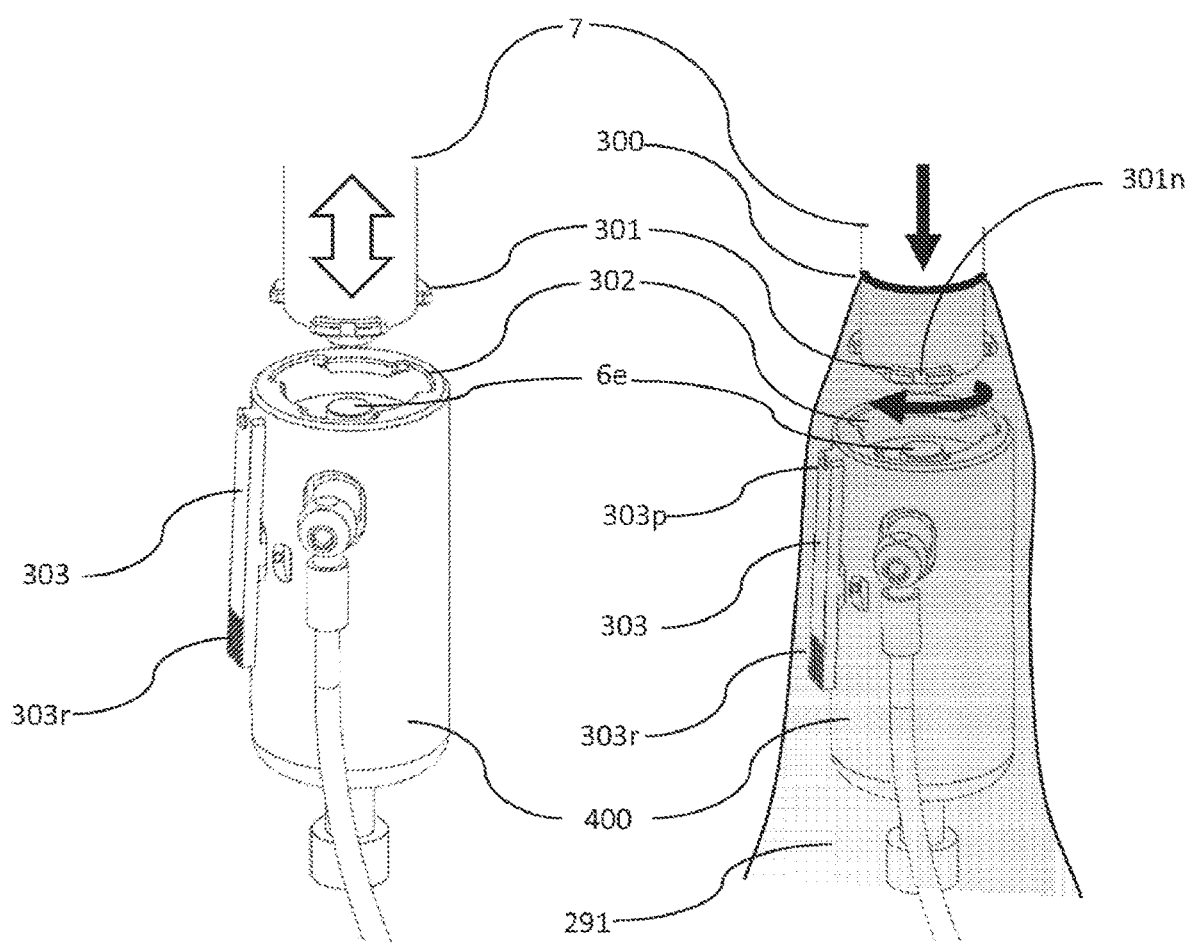
FIGS. 29a and 29b show a detailed embodiment of an interface to attach and remove the distal arm from the locking mechanism as depicted in FIG. 28b.

A screw thread, such as shown in FIG. 26a and FIG. 26b may be used for detachment of the distal portion of the arm from the actuator. FIG. 29a and FIG. 29b detail another embodiment of a detachment mechanism between the distal arm portions and proximal base that is well suited for a base arm drape (291). A series of tabs (301) on the base arm segment (7) matches a series of slots (302) on the actuator unit (400). The base arm segment (7) is pushed towards the actuator (6), and once the tabs (301) clear the slots (302), the base arm segment (7) and actuator (400) are rotated relative to each other. Rotation is allowed until the pin (303p) on the spring-loaded push release lever (303) mates to the notch (301n) on one of the tabs (301). At this point, further rotation is prevented and the actuator (400) and base arm segment (7) are locked together. It is advantageous to retract the actuator extension (6e) so that excessive force does not need to be deployed in the mating process between the actuator (400) and the base arm segment (7). To release the actuator (400) from the base arm segment (7), the release tab (303r) is pushed so that the pin (303p) releases from the notch (301n). The base arm segment (7) and the actuator (400) are then rotated relative to each other such that the tabs (301) and slots (302) line up, and subsequently the base arm segment (7) can be extracted from the actuator (400). In this embodiment, the sterile drape (291) may be taped (300) to the base arm segment (7) above the distal tabs (301), prior to attaching the base arm segment (7) to the actuator (400) as seen in FIG. 29b. The sterile drape (291) may also be attached to the base arm segment (7) or actuator (400) by other means.

Other than the ability to sterilize the portion of the arm distal to the actuator (400), there are other interesting aspects of having the distal portions of the arm removable from the actuator (400) as shown in FIG. 28b and FIG. 29. The portion of the arm distal to the actuator (400) comprises only mechanical parts (tubes, rods, slugs, joints, etc.), and thus can be fabricated out of disposable plastic materials for one time (or limited time use) in the operating room. This can be useful in certain surgical procedures where it is desired to dispose of the distal portions of the arm after each use while retaining/reusing the actuator (400) and base (1) (20) that provide the locking and unlocking power. Another interesting aspect is that distal arm linkages of different lengths and sizes can be attached to the same actuator (400 and base (1)(20), enabling users to customize the arm system for a particular surgical application.

It is also possible for portions of the arm distal to the actuator (400) to be radiolucent. This is particularly useful in medical applications where x-ray imaging modalities may be used in conjunction with a procedure where instruments (10) must be held steady. Materials such as carbon fiber, which do not interfere with x-rays, can be used to fabricate the portions of the arm distal to the actuator (400). The actuator (400) and parts proximal to the actuator may still contain metallic or high density components, since these components are not close to the imaging target (and instrument being held) and thus will not interfere with x-ray imaging. For example, in FIG. 28b and FIG. 29, the entire portion of the arm distal to the actuator (400) could be made of radiolucent material choices. Alternatively, the center rotational joint (30) could contain radiopaque materials, and only the distal arm segment (8), distal spherical joint (32), distal rotational joint (33), instrument holder (10), and other components distal to the center rotational joint (30) could be made of radiolucent materials.

In some embodiments it may be useful to include a counter-balance to compensate for at least some of the arm's weight and/or the weight of the instrument (10). This helps relieve the user from struggling against the weight of the arm and/or instrument when positioning and maneuvering the instrument. The general problem is taking stored energy from a spring to compensate for a change in potential energy as the position of the arm changes. While a full counter balance design is possible that compensates for the entire weight of the arm and/or instrument, a simpler and still useful implementation is to counter balance only the proximal arm linkage (335), including the actuator (400) and the base arm segment (7). The reason is that the nominal arm embodiments (FIGS. 1-4) have at least 7 degrees of freedom which means that for an arbitrary placement of the instrument (10) in 3D space, the central rotational joint (30) is still freely able to swivel. Adding a counter balance to compensate for the weight of the proximal arm linkage (335) can enable the proximal arm linkage (335) and central rotational joint (30) to "float" in an arbitrary position in space and not "fall" under the weight of gravity when not being supported by a hand.

Figure 30:
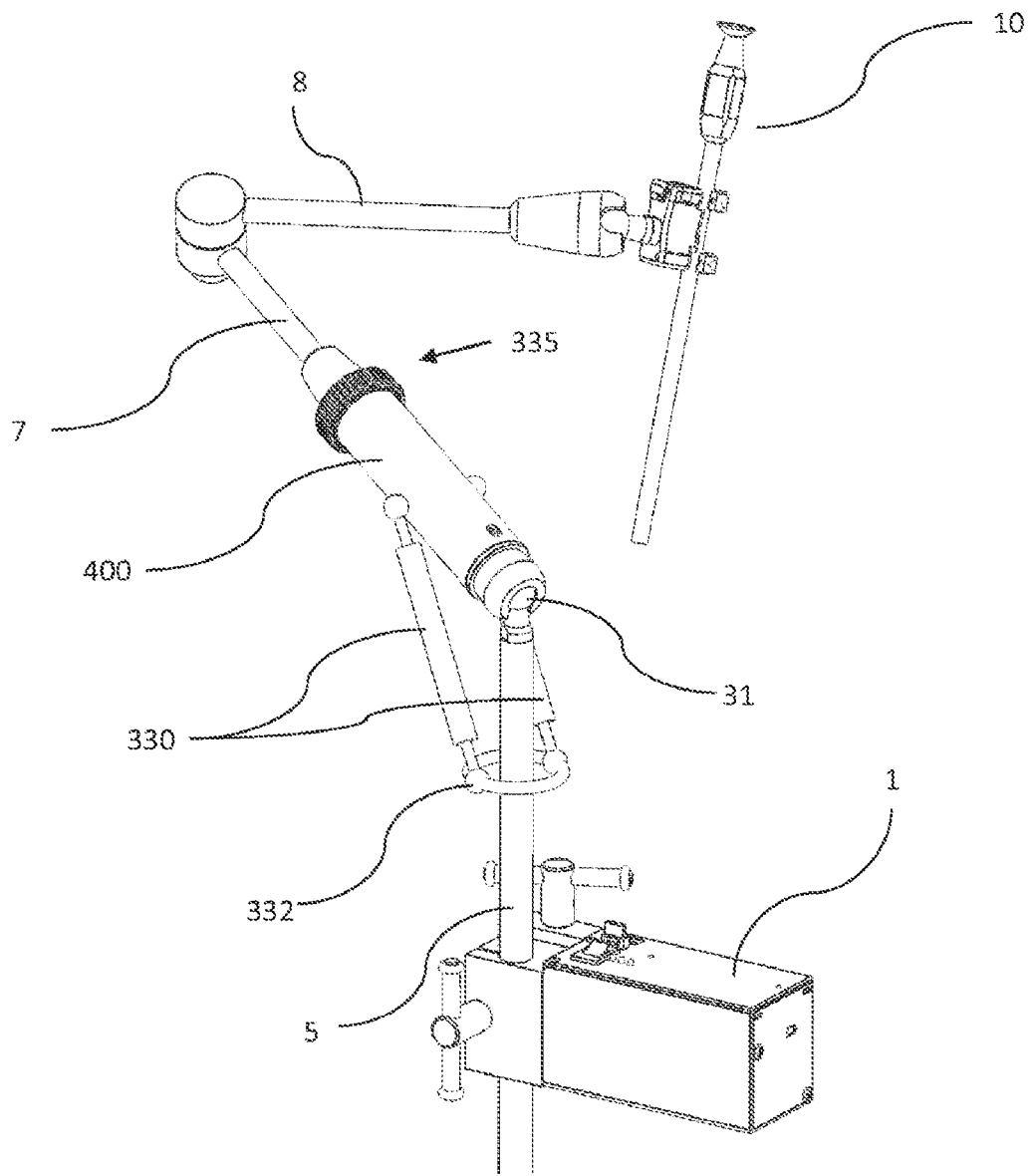
FIG. 30 shows an embodiment for a proximal arm linkage counter balance system for use in a repositionable, lockable support arm in accordance with the present invention.

Referring to FIG. 30, one method of counterbalancing the proximal arm linkage (335) is to use a set of compression springs (330) straddling the base spherical joint (31). To accommodate the base spherical joint (33) rotation about the pole (5) axis, a means must be provided to position the springs (330) as the joint (33) rotates. This is depicted by a ring (332). Not shown are the elements needed to rotate the ring as the arm moves.

Figure 31:
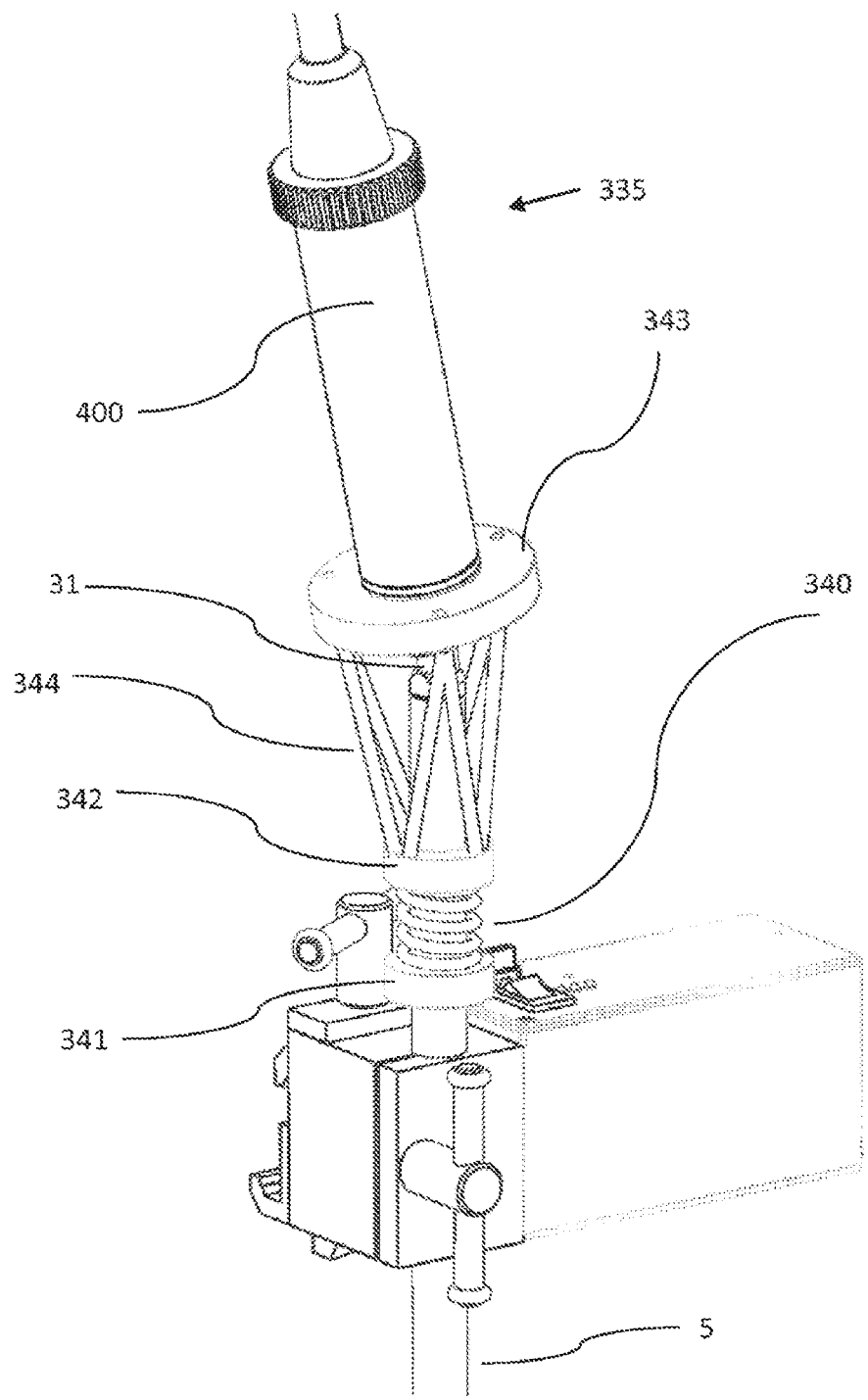
FIG. 31 shows an alternate octahedron embodiment for a proximal arm linkage counter balance system for use in a repositionable, lockable support arm in accordance with the present invention.

Another novel counter balance means is to put a compressive spring element (340) around the pole (5) as depicted in FIG. 31. The bottom of the spring (340) pushes against a lower ring (341) fixed to the pole. An upper ring (342) is free to translate up and down on the pole, compressing the spring (340) according to the spring's displacement. The spring (340) is compressed as a direct result of the proximal arm linkage (335) deviating from vertical. The angular motion of the proximal arm linkage (335) is conveyed by 6 link members (344) connected to a ring (343) attached to the proximal arm linkage (335) above the base spherical joint (31). This set of links (344) forms an octahedron which compensates for gravity on the proximal arm linkage (335) based the angle of the base spherical joint (31) with respect to vertical.

Figure 32A:
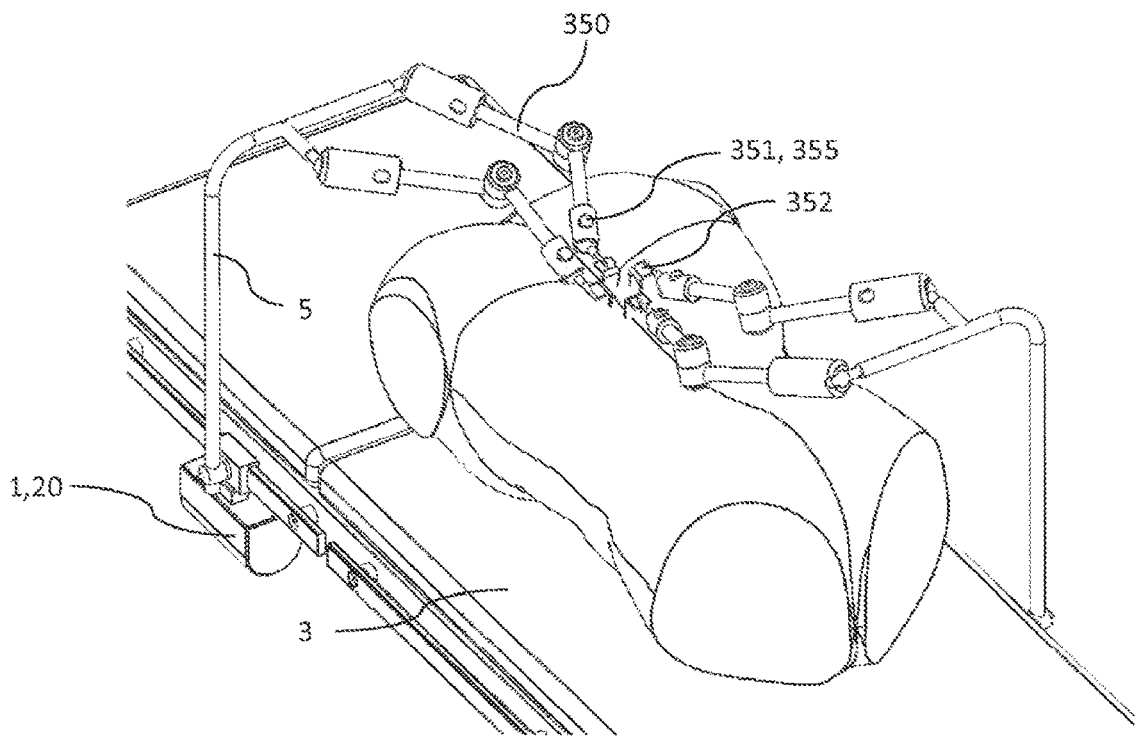
FIGS. 32a and 32b show a retraction system comprised of multiple repositionable, lockable retractor support arms in accordance with the present invention.
Figure 32B:
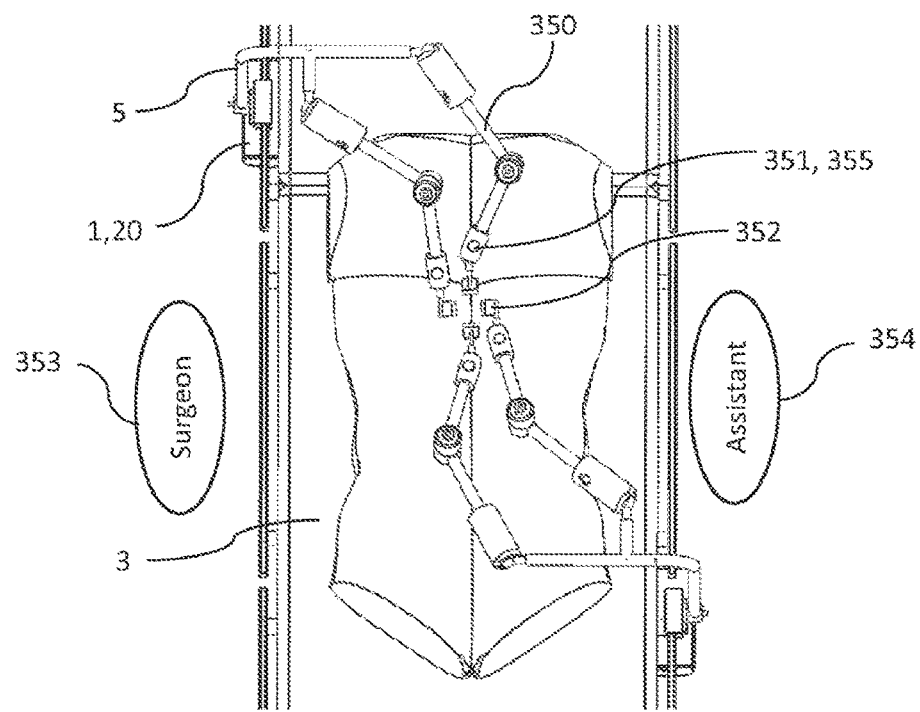
Figure 33:
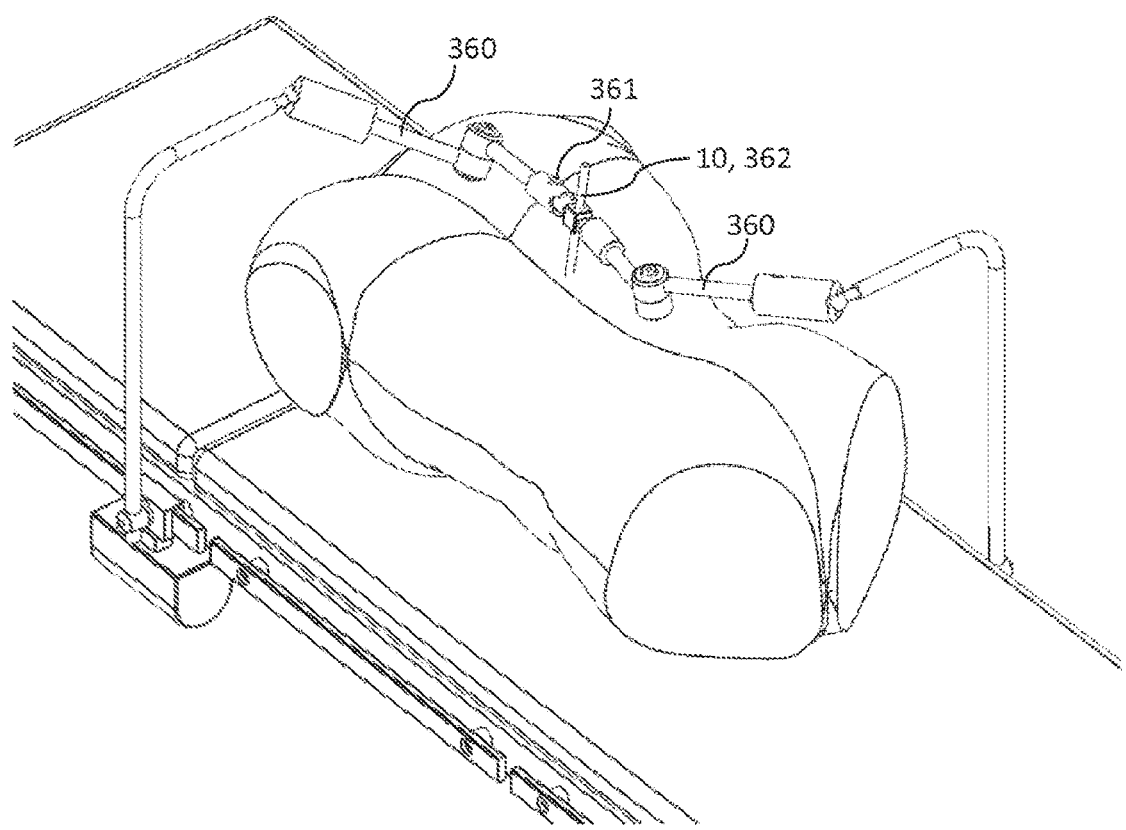
FIG. 33 shows an instrument positioning system with increased strength and stability by operating multiple repositionable, lockable support arms in parallel.

It is a well-known problem in surgery that applying retraction forces for long periods of time can result in tissue damage or necrosis. Therefore, it is suggested that retractor blades are periodically released throughout the surgical procedure. However, with existing retraction systems, release of retractor blades takes significant time which is very costly in the operating room. The system in FIG. 32 which leverages the locking arm technology herein addresses this problem since each retractor blade can be independently released and repositioned within a matter of seconds. In one embodiment of the retraction system, one or more arms are deployed (350) to hold one or more retractor blades (352), each arm with an independent lock/unlock button or switch (351) preferably located near the distal end of the arms. It is advantageous for each arm (350) to be deployed from the superior or inferior direction of the table (3) as shown so that the surgeon (353) and assistant (354) have ample space to operate. More than one arm (350) can be attached to a single pole (5), and multiple arms can share the same base unit (1)(20) as applicable.

In one embodiment of the retraction system shown in FIG. 35, an electronic system controller (not shown) alerts the user to move each respective arm (350) after a certain period of time has elapsed (for example, 20-30 minutes). The alert can be in the form of a sound, blinking light, steady light, or other means. Each arm can have one or more LED lights attached to it (355), preferably co-located with the lock/unlock button (351). The controller can change the light (355) state, e.g. from green to red or from off to on, when retraction time for each respective arm has reached a threshold. Once the arm (350) is released, repositioned, and relocked, the controller can reset the timer and light state (e.g. red to green or on to off). In another embodiment, there may be force sensors, blood flow sensors, or other sensors attached to the arms (not shown) that indicate retraction force or tissue state. Once these sensors indicate that the tissue is in danger (e.g. low blood flow, or excessive force over a certain period of time), the controller can alert the user to move the retractor blade (352) using means described above. Once moved, the arm (350) alerts the controller that the tissue is safe again, and monitoring/timers can reset. Note that the retraction alert system described herein can also apply to retraction systems that do not utilize the automatic locking arm described in this application.

In another embodiment of a locking arm system (FIG. 36), two or more arms (360) are used in parallel to hold the same instrument (10). Two or more arms in parallel significantly increases the overall stiffness of the arm system, further minimizing any motion of the instrumentation (10) being held under load. Two arms can be controlled with the same actuation button or switch (361), locking and unlocking both arms (360) simultaneously for ease of use. In the particular scenario shown in FIG. 36, two arms can hold a single tube (362) for pedicle screw placement during spine surgery to ensure maximum strength and stiffness during screw drilling, tapping, and insertion.

Modification of the above-described assemblies and methods for carrying out the invention, combinations between different variations as practicable, and variations of aspects of the invention that are obvious to those of skill in the art are intended to be within the scope of the invention disclosure.

What is claimed is:
1. A lockable support assembly comprising:
 a base arm having a lower end and an upper end;
 a distal arm having a proximal end and a distal end;
 a center joint directly or indirectly linking the upper end of the base arm to the proximal end of the distal arm;
 a lower joint at the lower end of the base arm;
 an upper joint at the distal end of the distal arm; and
 an electrically powered electromechanical locking actuator disposed within the base arm between the lower end and the upper end, the powered electromechanical locking actuator configured to simultaneously engage the lower joint, the center joint, and the upper joint to deliver locking forces to the lower joint, the center joint, and the upper joint.
2. An assembly as in claim 1, further comprising a latching mechanism that prevents the powered electromechanical locking actuator from disengaging upon loss of power to the powered locking actuator.

3. An assembly as in claim 2, wherein the latching mechanism comprises a non-backdrivable lead screw mechanism which maintains its position when power is lost.

4. An assembly as in claim 1, wherein the powered electromechanical locking actuator comprises a force generator comprising a motor which is coupled by a lead screw to deliver forces to the center joint, the lower joint, and the upper joint.

5. An assembly as in claim 1, wherein the base arm is separable from the powered electromechanical locking actuator to allow removal of the base arm, distal arm, and center and upper joints to permit sterilization or replacement of the base arm, distal arm, and center and upper joints.

6. An assembly as in claim 1, further comprising a lock/unlock button or switch disposed near a distal end of the distal arm to enable one-handed instrument manipulation and unlocking/locking.

7. A lockable support assembly comprising:
a base arm having a lower end and an upper end;
a distal arm having a proximal end and a distal end;
a center joint directly or indirectly linking the upper end of the base arm to the proximal end of the distal arm;
a lower joint at the lower end of the base arm;
an upper joint at the distal end of the distal arm; and
an electrically powered electromechanical locking actuator configured to simultaneously engage the lower joint, the center joint, and the upper joint to deliver locking forces to prevent relative motion of the base arm and the distal arm;
wherein the powered electromechanical locking actuator is disposed within the base arm between the lower end and the upper end.

8. An assembly as in claim 7, wherein the powered electromechanical locking mechanism comprises a force generator which transmits a locking force through the base arm and the distal arm to lock the joints.

9. An assembly as in claim 8, wherein the force generator comprises a motor which is coupled by a lead screw to deliver forces to the center, lower and upper joints.

10. An assembly as in claim 7, further comprising a lock/unlock button or switch disposed near a distal end of the distal arm to enable one-handed instrument manipulation and unlocking/locking.

11. An assembly as in claim 7, wherein at least some of the lower joint, the center joint, and the upper joint are biased to reduce clearances in the respective joint or powered locking actuator in the absence of locking forces to prevent an unintended change of arm position as the powered locking actuator engages the joints.

12. A lockable support assembly comprising:
a base arm extending along a first longitudinal axis between a lower end and an upper end;
a distal arm having a proximal end and a distal end;
a central joint directly or indirectly linking the upper end of the base arm to the proximal end of the distal arm;
a lower joint at the lower end of the base arm;
an upper joint at the distal end of the distal arm; and
an electrically powered electromechanical locking actuator disposed within the base arm at a location between the lower joint and the central joint, the powered electromechanical locking actuator configured to control locking of the lockable support assembly by delivering locking forces to the lower joint, to the central joint, and to the upper joint.

13. The lockable support assembly of claim 12, wherein each of the central joint, the lower joint, and the upper joint include a locking mechanism to receive the locking forces delivered by the power electromechanical locking actuator and lock respective joints in response to receiving the locking forces.

14. The lockable support assembly of claim 12, wherein the power electromechanical locking actuator includes a bi-lateral force generator to simultaneously deliver the locking forces to the lower joint, the central joint and the upper joint.

15. The lockable support assembly of claim 14, wherein the powered electromechanical locking actuator further comprises an upper base rod which transmits the locking force from one side of the bilateral force generator to the central joint and a distal rod which transmits the locking force from the central joint to the upper joint.

16. The lockable support assembly of claim 15, wherein the powered electromechanical locking actuator further comprises a lower base rod which transmits force from an opposite side of the bilateral force generator to the lower joint.

17. The lockable support assembly of claim 12, wherein the central joint comprises a rotational joint having an axle joining the upper end of the base arm to the proximal end of the distal arm and wherein an interface surface at the upper end of the base arm frictionally engages an interface surface on the proximal end of the distal arm such that the powered electromechanical locking actuator drives the interface surfaces together to prevent relative movement of the arms.

18. The lockable support assembly of claim 17, wherein the rotational joint further comprises a first inclined surface which receives force from the upper base rod and a second inclined surface which transmits force to the distal rod, wherein the aligned surfaces are coupled by the axle which both (1) locks the interface surfaces together; and (2) translates the second inclined surface in response to the upper base rod engaging the first inclined surface.

19. The lockable support assembly of claim 12, wherein the lower joint and the upper joint each comprise spherical joints including a friction block which is coupled to a bilateral force generator to lock the spherical joints when the generator generates a locking force.

20. The lockable support assembly of claim 12, wherein the power electromechanical locking actuator comprises a bilateral force generator which transmits a locking force in one axial direction to the lower joint and in an opposite axial direction to the central joint and the upper joint, the bilateral force generator including a lead screw driven by a motor and a follower which travels over the screw.

* * * * *

UNITED STATES PATENT AND TRADEMARK OFFICE
CERTIFICATE OF CORRECTION

PATENT NO. : 11,179,222 B2  
APPLICATION NO. : 16/877023  
DATED : November 23, 2021  
INVENTOR(S) : Schlosser et al.

Page 1 of 1

It is certified that error appears in the above-identified patent and that said Letters Patent is hereby corrected as shown below:

On the Title Page

In item (57), in "Abstract", in Column 2, Line 13, delete "kicking" and insert --locking-- therefor On page 5, in Column 2, under "Other Publications", Line 12, delete "Reconstruciton." and insert --Reconstruction.-- therefor Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*